(12) United States Patent
Fatheree et al.

(10) Patent No.: US 7,341,993 B2
(45) Date of Patent: Mar. 11, 2008

(54) CROSS-LINKED GLYCOPEPTIDE—CEPHALOSPORIN ANTIBIOTICS

(75) Inventors: Paul R. Fatheree, San Francisco, CA (US); Martin S. Linsell, San Francisco, CA (US); Daniel D. Long, San Francisco, CA (US); Daniel Marquess, Half Moon Bay, CA (US); Edmund J. Moran, San Francisco, CA (US); Matthew B. Nodwell, San Francisco, CA (US); S. Derek Turner, Pacifica, CA (US); James Aggen, Burlingame, CA (US)

(73) Assignee: Theravance, Inc., South San Francisco, CA (US)

( * ) Notice: Subject to any disclaimer, the term of this patent is extended or adjusted under 35 U.S.C. 154(b) by 22 days.

(21) Appl. No.: 11/172,303

(22) Filed: Jun. 30, 2005

(65) Prior Publication Data

US 2005/0239691 A1 Oct. 27, 2005

Related U.S. Application Data

(63) Continuation of application No. 10/269,471, filed on Oct. 11, 2002, now Pat. No. 6,974,797.

(60) Provisional application No. 60/328,889, filed on Oct. 12, 2001.

(51) Int. Cl.
  *A61K 38/16* (2006.01)
  *A61K 38/00* (2006.01)
(52) U.S. Cl. .............................. 514/8; 514/2; 514/201; 514/202; 514/206
(58) Field of Classification Search ...................... 514/8
  See application file for complete search history.

(56) References Cited

U.S. PATENT DOCUMENTS

| 4,220,761 | A |   | 9/1980  | Takaya et al. |
|---|---|---|---|---|
| 4,341,775 | A |   | 7/1982  | Takaya et al. |
| 4,366,153 | A |   | 12/1982 | Takaya et al. |
| 4,427,677 | A |   | 1/1984  | Takaya et al. |
| 4,487,767 | A |   | 12/1984 | Takaya et al. |
| 4,550,102 | A |   | 10/1985 | Teraji et al. |
| 4,603,129 | A | * | 7/1986  | Blumbach et al. .......... 514/206 |
| 4,647,556 | A | * | 3/1987  | Lattrell et al. ............... 514/206 |
| 4,667,028 | A | * | 5/1987  | Schwab et al. ............. 540/222 |
| 4,668,783 | A | * | 5/1987  | Ochiai et al. ............... 540/222 |
| 4,840,945 | A | * | 6/1989  | Ohnishi et al. ............. 514/206 |
| 4,921,851 | A |   | 5/1990  | Kishimoto et al. |
| 4,943,567 | A |   | 7/1990  | Nishizawa et al. |
| 5,071,979 | A |   | 12/1991 | Lattrell et al. |
| 5,693,791 | A |   | 12/1997 | Truett et al. |
| 6,437,119 | B1 |  | 8/2002  | Truett |
| 6,878,686 | B2 | * | 4/2005  | Marquess et al. .......... 514/8 |
| 6,974,797 | B2 | * | 12/2005 | Fatheree et al. ............... 514/8 |
| 6,995,138 | B2 | * | 2/2006  | Marquess et al. ............... 514/8 |
| 2004/0033939 | A1 |  | 2/2004  | Marquess et al |
| 2004/0266666 | A1 |  | 12/2004 | Fatheree et al. |
| 2005/0026818 | A1 |  | 2/2005  | Fatheree et al. |

FOREIGN PATENT DOCUMENTS

| GB | 2 033 377 A | 5/1980 |
|---|---|---|
| JP | 60-41682 | 3/1985 |
| WO | WO 97/41128 | * 11/1997 |
| WO | WO 99/42476 | 8/1999 |
| WO | WO 99/64049 A1 | 12/1999 |
| WO | WO 00/39156 | 7/2000 |

OTHER PUBLICATIONS http://cancerweb.ncl.ac.uk/cgi-bin/omd?query=phenylene.*
http://en.wikipedia.org/wiki/Substitution_reaction.*
http://en.wikipedia.org/wiki/Functional_group.*
U.S. Appl. No. 09/457,926, filed Dec. 8, 1999, Christensen et al.
Boeckh, M. et al., "Pharmacokinetics and Serum Bactericidal Activity of Vancomycin Alone and in Combination with Ceftazidime in Healthy Volunteers." Antibacterial Agents and Chemotherapy, vol. 32. No. 1, pp. 92-95 (1988).
Hammes, W. P., "Biosynthesis of peptidoglycan in *Gaffkya homari*. The mode of action of penicillin G and mecillinam", Chemical Abstracts, vol. 86, No. 5, Abstract No. 26406 (Jan. 31, 1977).
Kim, M. et al., "Synthesis and Antibacterial Activity of Cephalosporins Having Hydroxamic Acid at C-7 Position." Biorganic & Med. Chem. Letters, vol. 6, No. 17, pp. 2077-2080 (1996).
Lattrell, R. et al., "Synthesis and Structure-Activity Relationships in the Cefpirome Series." Journal of Antibiotics, vol. XLI, No. 10, pp. 1374-1394.
Rao, J. et al., "Tight Binding of a Dimeric Derivative of Vancomycin with Dimeric L-Lys-D-Ala-D-Ala." J. Am. Chem. Soc., vol. 119, pp. 10286-10290 (1997).
Renoud-Grappin, M. et al., "Imidazo[1,5-b]pyridazine-d4T conjugates:synthesis and anti-human Immunodeficiency virus evaluation." Antiviral Chemistry & Chemotherapy, vol. 9, pp. 205-223.
Staroske, T. et al., "Synthesis of Covalent Head-to-Tail Dimers of Vancomycin." Tetrahedron Letters 39, pp. 4917-4920 (1998).
Sundram, U. et al., "General and Efficient Method for the Solution- and Solid-Phase Synthesis of Vancomycin Carboxamide Derivatives." J. Org. Chem., vol. 60, pp. 1102-1103 (1995).
Sundram, U. et al., "Novel Vancomycin Dimers with Activity against VAncomycin-Resistant Enterococci" J. Am. Chem. Soc., vol. 118, pp. 13107-13108 (1996).

* cited by examiner

*Primary Examiner*—Cecilia J. Tsang
*Assistant Examiner*—Maury Audet
(74) *Attorney, Agent, or Firm*—Jeffrey A. Hagenah

(57) ABSTRACT

This invention provides cross-linked glycopeptide-cephalosporin compounds and pharmaceutically acceptable salts thereof which are useful as antibiotics. This invention also provides pharmaceutical compositions containing such compounds; methods for treating bacterial infections in a mammal using such compounds; and processes and intermediates useful for preparing such compounds.

2 Claims, No Drawings

CROSS-LINKED GLYCOPEPTIDE—CEPHALOSPORIN ANTIBIOTICS

CROSS-REFERENCE TO RELATED APPLICATIONS

This application is a continuation of U.S. application Ser. No. 10/269,471, filed Oct. 11, 2002 now U.S. Pat. No. 6,974,797; which application claims the benefit of U.S. Provisional Application No. 60/328,889, filed on Oct. 12, 2001; the entire disclosure of which is incorporated herein by reference in its entirety.

BACKGROUND OF THE INVENTION

1. Field of the Invention

This invention is directed to novel cross-linked vancomycin-cephalosporin compounds which are useful as antibiotics. This invention is also directed to pharmaceutical compositions comprising such compounds; methods of using such compounds as antibacterial agents; and processes and intermediates for preparing such compounds.

2. State of the Art

Various classes of antibiotic compounds are known in the art including, for example, β-lactam antibiotics, such as cephalosporins, and glycopeptide antibiotics, such as vancomycin. Cross-linked antibiotic compounds are also known in the art. See, for example, U.S. Pat. No. 5,693,791, issued to W. L. Truett and entitled "Antibiotics and Process for Preparation"; and WO 99/64049 A1, published on Dec. 16, 1999, and entitled "Novel Antibacterial Agents."

Despite such compounds, a need exists for new antibiotics having improved properties including, by way of example, increased potency against gram-positive bacteria. In particular, a need exists for new antibiotics which are highly effective against antibiotic-resistant strains of bacteria, such as methicillin-resistant *Staphylococci aureus* (MRSA) and methicillin-resistant *Staphylococci epidermitis* (MRSE).

SUMMARY OF THE INVENTION

The present invention provides novel cross-linked glycopeptide—cephalosporin compounds which are useful as antibiotics. Among other properties, compounds of this invention have been found to possess surprising and unexpected potency against gram-positive bacteria including methicillin-resistant *Staphylococci aureus* (MRSA) and methicillin-resistant *Staphylococci epidermitis* (MRSE).

Accordingly, in one of its composition aspects, this invention provides a compound of formula I:

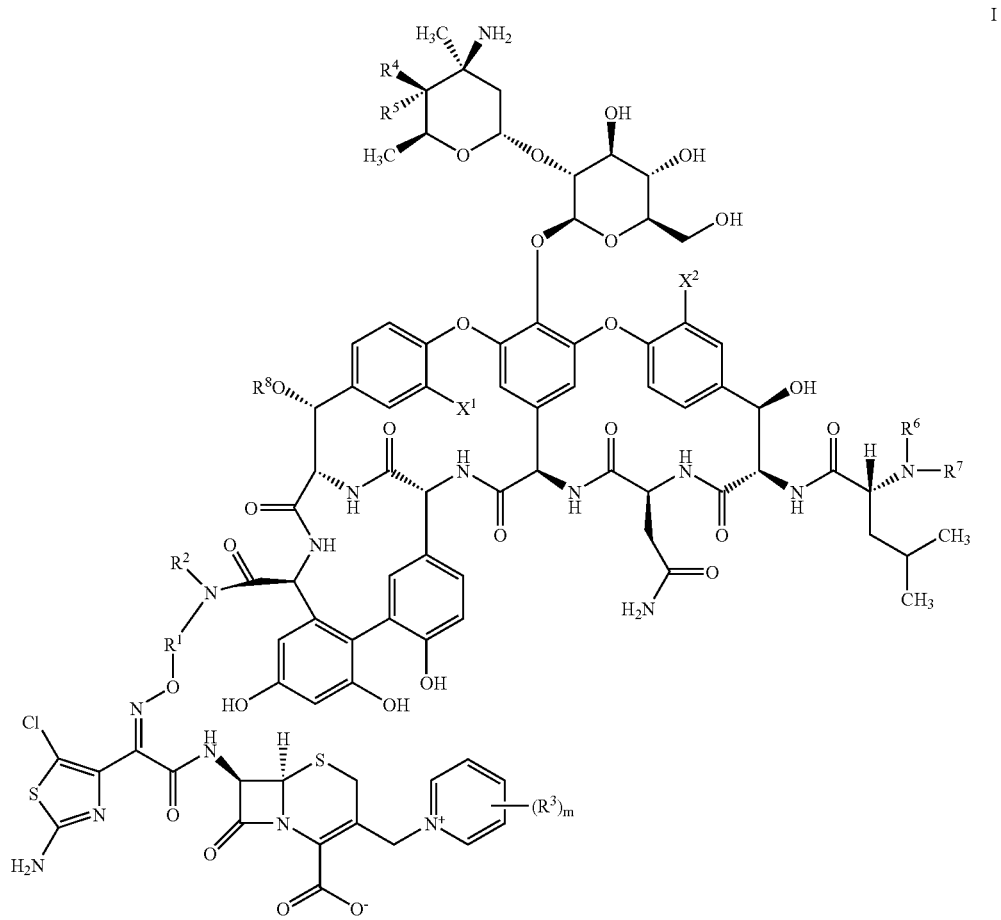

or a pharmaceutically-acceptable salt thereof, wherein $X^1$ and $X^2$ are independently selected from the group consisting of hydrogen and chloro;

$R^1$ is —$Y^a$—(W)$_n$—$Y^b$—;

W is selected from the group consisting of —O—, —N($R^d$)—, —S—, —S(O)—, —S(O)$_2$—, $C_{3-6}$ cycloalkylene, $C_{6-10}$ arylene and $C_{2-9}$ heteroarylene; wherein each arylene, cycloalkylene and heteroarylene group is optionally substituted with 1 to 3 substituents independently selected from $R^b$;

$Y^a$ and $Y^b$ are independently $C_{1-5}$ alkylene, or when W is cycloalkylene, arylene or heteroarylene, $Y^a$ and $Y^b$ are independently selected from the group consisting of a covalent bond and $C_{1-5}$ alkylene; wherein each alkylene group is optionally substituted with 1 to 3 substituents independently selected from —$OR^d$, —$NR^dR^e$, —$CO_2R^d$, —$C(O)NR^dR^e$ and —$S(O)_2NR^dR^e$;

$R^2$ is hydrogen or $C_{1-6}$ alkyl;

each $R^3$ is independently selected from the group consisting of $C_{1-6}$ alkyl, $C_{2-6}$ alkenyl, $C_{2-6}$ alkynyl, $C_{3-6}$ cycloalkyl, $C_{6-10}$ aryl, $C_{2-9}$ heteroaryl, $C_{3-6}$ heterocyclic and $R^a$; or two adjacent $R^3$ groups are joined to form $C_{3-6}$ alkylene or —O—($C_{1-6}$alkylene)—O—; wherein each alkyl, alkylene, alkenyl and alkynyl group is optionally substituted with 1 to 3 substitutents independently selected from the group consisting of $R^a$ and $R^c$; and each aryl, cycloalkyl, heteroaryl and heterocyclic group is optionally substituted with 1 to 3 substitutents independently selected from the group consisting of $R^b$;

one of $R^4$ and $R^5$ is hydroxy and the other is hydrogen;

$R^6$ and $R^7$ are independently hydrogen or methyl;

$R^8$ is hydrogen or a group of formula (i):

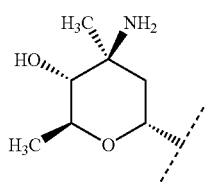
(i)

each $R^1$ is independently selected from the group consisting of —$OR^d$, halo, —$SR^d$, —$S(O)R^d$, —$S(O)_2R^d$, —$S(O)_2OR^d$, —$S(O)_2NR^dR^e$, —$NR^dR^e$, —$CO_2R^d$, —$OC(O)R^d$, —$C(O)NR^dR^e$, —$NR^dC(O)R^e$, —$OC(O)NR^dR^e$, —$NR^dC(O)OR^e$, —$NR^dC(O)NR^dR^e$, —$CF_3$ and —$OCF_3$;

each $R^b$ is independently selected from the group consisting of $C_{1-6}$ alkyl, $C_{2-6}$ alkenyl, $C_{2-6}$ alkynyl and $R^a$;

each $R^c$ is independently selected from the group consisting of $C_{3-6}$ cycloalkyl, $C_{6-10}$ aryl, $C_{2-9}$ heteroaryl and $C_{3-6}$ heterocyclic; wherein each cycloalkyl, aryl, heteroaryl and heterocyclic group is optionally substituted with 1 to 3 substituents independently selected from the group consisting of $C_{1-6}$ alkyl and $R^f$;

each $R^d$ and $R^e$ is independently selected from the group consisting of hydrogen, $C_{1-6}$ alkyl, $C_{2-6}$ alkenyl, $C_{2-6}$ alkynyl, $C_{3-6}$ cycloalkyl, $C_{6-10}$ aryl, $C_{2-9}$ heteroaryl and $C_{3-6}$ heterocyclic; or $R^d$ and $R^e$ are joined, together with the atoms to which they are attached, to form a $C_{3-6}$ heterocyclic ring having 1 to 3 heteroatoms independently selected from oxygen, nitrogen or sulfur; wherein each alkyl, alkenyl and alkynyl group is optionally substituted with 1 to 3 substituents independently selected from the group consisting of $R^c$ and $R^f$; and each aryl, cycloalkyl, heteroaryl and heterocyclic group is optionally substituted with 1 to 3 substituents independently selected from the group consisting of $C_{1-6}$ alkyl and $R^f$;

each $R^f$ is independently selected from the group consisting of —OH, —$OC_{1-6}$ alkyl, —$SC_{1-6}$ alkyl, —F, —Cl, —$NH_2$, —$NH(C_{1-6}$ alkyl), —$N(C_{1-6}$ alkyl)$_2$, —$OC(O)C_{1-6}$ alkyl, —$C(O)OC_{1-6}$ alkyl, —$NHC(O)C_{1-6}$ alkyl, —$C(O)OH$, —$C(O)NH_2$, —$C(O)NHC_{1-6}$ alkyl, —$C(O)N(C_{1-6}$ alkyl)$_2$, —$CF_3$ and —$OCF_3$;

m is 0, 1, 2 or 3; and n is 0 or 1.

This invention is also directed to intermediates useful for preparing compounds of formula I, and salts thereof. Accordingly, in another of its composition aspects, this invention provides a compound of formula II:

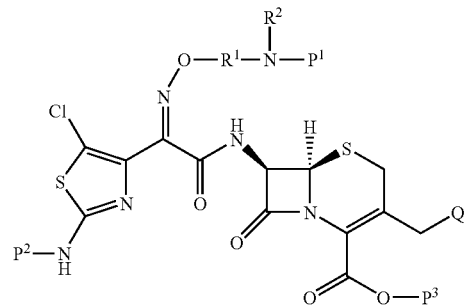
II or a salt thereof; wherein $R^1$ and $R^2$ are as defined herein;

$P^1$ and $P^2$ are independently hydrogen or an amino-protecting group;

$P^3$ is hydrogen or a carboxy-protecting group;

Q is a leaving group or a group of the formula:

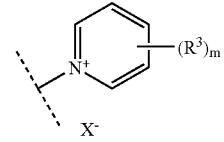

where $R^3$ and m are as defined herein; and $X^-$ is an optionally present anion; which compounds are useful as intermediates for preparing compounds of formula I and/or as antibiotics.

In yet another of its composition aspects, this invention provides a compound of formula III:

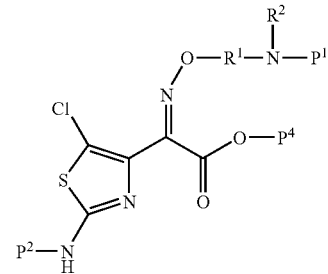
III or salts thereof; wherein $R^1$, $R^2$, $P^1$ and $P^2$ are as defined herein, and $P^4$ is hydrogen or a carboxy-protecting group; which compounds are useful as intermediates for preparing compounds of formula I or II.

In separate and distinct composition aspects, this invention also provides compounds of formulae 2, 5b, 7, 8, 10, 11 and 13 as defined herein, or salts or protected derivatives thereof; which compounds are useful as intermediates for preparing compounds of formula I and/or as antibiotics.

In another of its composition aspects, this invention provides a pharmaceutical composition comprising a pharmaceutically-acceptable carrier and a therapeutically effective amount of a compound of formula I, or a pharmaceutically-acceptable salt thereof.

While not intending to be limited by theory, the compounds of formula I are believed to inhibit bacterial cell wall biosynthesis thereby inhibiting the growth of the bacteria or causing lysis of the bacteria. Therefore, among other properties, the compounds of formula I are useful as antibiotics.

Accordingly, in one of its method aspects, this invention provides a method of treating a bacterial infection in a mammal, the method comprising administering to a mammal a pharmaceutical composition comprising a pharmaceutically-acceptable carrier and a therapeutically effective amount of a compound of formula I, or a pharmaceutically-acceptable salt thereof.

Additionally, in another of its method aspects, this invention provides a method of inhibiting the growth of bacteria, the method comprising contacting bacteria with a growth-inhibiting amount of a compound of formula I, or a pharmaceutically-acceptable salt thereof.

In yet another of its method aspects, this invention provides a method of inhibiting bacterial cell wall biosynthesis, the method comprising contacting bacteria with a cell wall biosynthesis-inhibiting amount of a compound of formula I, or a pharmaceutically-acceptable salt thereof.

This invention is also directed to processes for preparing compounds of formula I or a salt thereof. Accordingly, in another of its method aspects, this invention provides a process for preparing a compound of formula I, or a salt thereof; the process comprising:

(a) reacting a glycopeptide of formula 1 as defined herein, with a compound of formula 2 as defined herein; or (b) reacting a compound of formula 10 as defined herein, with a compound of formula 11 as defined herein; or (c) reacting a compound of formula 9 as defined herein, with a compound of formula 13 as defined herein;

to provide a compound of formula I or a salt thereof. In one preferred embodiment, the above process further comprises the step of forming a pharmaceutically-acceptable salt of a compound of formula I. This invention is also directed to the product prepared by any of these processes.

This invention is also directed to a compound of formula I, or a pharmaceutically-acceptable salt thereof, for use in therapy. Additionally, this invention is directed to the use of a compound of formula I, or a pharmaceutically-acceptable salt thereof, for the manufacture of a medicament for the treatment of a bacterial infection in a mammal.

DETAILED DESCRIPTION OF THE INVENTION

This invention provides novel glycopeptide-cephalosporin compounds of formula I or pharmaceutically-acceptable salts thereof. These compounds have multiple chiral centers and, in this regard, the compounds are intended to have the stereochemistry shown. In particular, the glycopeptide portion of the compound is intended to have the stereochemistry of the corresponding naturally-occurring glycopeptide (i.e., vancomycin, chloroorienticin A and the like). The cephalosporin portion of the molecule is intended to have the stereochemistry of known cephalosporin compounds. However, it will be understood by those skilled in the art that minor amounts of isomers having a different stereochemistry from that shown may be present in the compositions of this invention provided that the utility of the composition as a whole is not significantly diminished by the presence of such isomers.

Additionally, the linking portion of the compounds of this invention (i.e., $R^1$) may contain one or more chiral centers. Typically, this portion of the molecule will be prepared as a racemic mixture. If desired, however, pure stereoisomers (i.e., individual enantiomers or diastereomers) may be used or a stereoisomer-enriched mixture can be employed. All such stereoisomers and enriched mixtures are included within the scope of this invention.

In addition, compounds of this invention contain several acidic groups (i.e., carboxylic acid groups) and several basic groups (i.e., primary and secondary amine groups) and therefore, the compounds of formula I can exist in various salt forms. All such salt forms are included within the scope of this invention. Also, since the compounds of formula I contain a pyridinium ring, an anionic counterion for the pyridinium group may optionally be present including, but not limited to, halides, such as chloride; carboxylates, such as acetate; and the like.

Furthermore, it will be understood by those skilled in the art that labile or chemically unstable compounds which lack any utility due to their instability are not included within the scope of this invention. For example, it is preferred that compounds of formula I contain at least two carbon atoms between any oxygen (—O—), nitrogen (—N<) or sulfur (—S—) atoms in the —O—$R^1$—N($R^2$)— moiety, since when these atoms are separated by a single carbon atom the resulting compound (i.e., containing an acetal, hemiacetal, ketal, hemiketal, aminal, hemiamial or thioketal group and the like) may be hydrolytically unstable under acidic conditions.

PREFERRED EMBODIMENTS

In the compounds of formula I, the following substituents and values are preferred:

In a preferred embodiment, the present invention is directed to compounds of formula Ia:

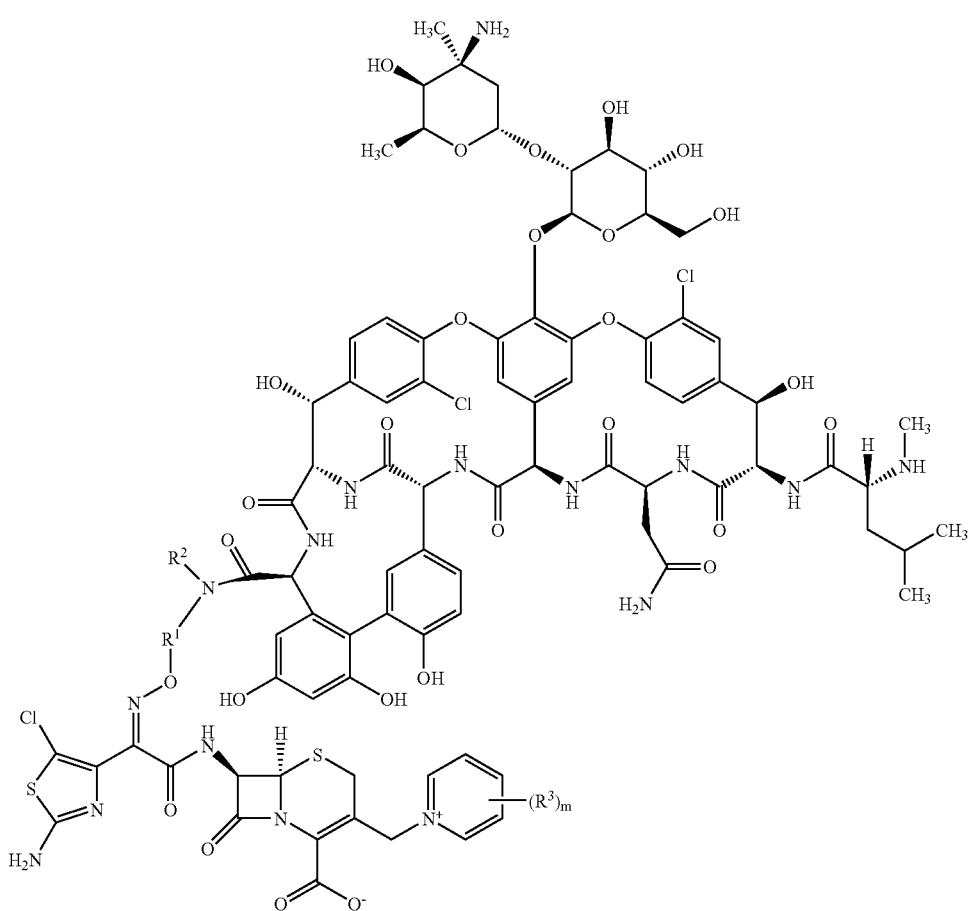

Ia or a pharmaceutically-acceptable salt thereof, wherein $R^1$, $R^2$, $R^3$ and m are as defined herein, including preferred embodiments.

In a preferred embodiment, $R^1$ is —$Y^a$—$Y^b$—, i.e., when n is 0. In this embodiment, $Y^a$ and $Y^b$ are independently $C_{1-5}$ alkylene groups wherein each alkylene group is optionally substituted with 1 to 3 substitutents independently selected from —$OR^d$, —$NR^dR^e$, —$CO_2R^d$, —$C(O)NR^dR^e$ and —$S(O)_2NR^dR^e$ as defined herein. Preferably, $Y^a$ and $Y^b$ are independently selected from $C_{1-3}$ alkylene; and more preferably, $C_{1-2}$ alkylene. More preferably, $Y^a$ and $Y^b$ are joined together (i.e., $R^1$) to form a —$(CH_2)_{2-8}$— group. Still more preferably, $Y^a$ and $Y^b$ are joined together to form a —$(CH_2)_2$—, —$(CH_2)_3$—, —$(CH_2)_4$—, —$(CH_2)_5$— or —$(CH)_6$— group. In a particularly preferred embodiment, $Y^a$ and $Y^b$ are joined together to form —$(CH_2)_3$— group.

In another preferred embodiment, $R^1$ is —$Y^a$—W—$Y^b$—, i.e., when n is 1. In this embodiment, $Y^a$ and $Y^b$ are independently $C_{1-5}$ alkylene, or when W is cycloalkylene, arylene or heteroarylene, $Y^a$ and $Y^b$ are independently selected from the group consisting of a covalent bond and $C_{1-5}$ alkylene. Each alkylene group in this embodiment is optionally substituted with 1 to 3 substituents selected from —$OR^d$, —$NR^dR^e$, —$CO_2R^d$, —$C(O)NR^dR^e$ and —$S(O)_2NR^dR^e$ as defined herein. When $Y^a$ or $Y^b$ is an alkylene group, the alkylene group is preferably a $C_{1-3}$ alkylene group; more preferably, a $C_{1-2}$ alkylene group; still more preferably, a —$(CH_2)_{1-2}$— group. In a particularly preferred embodiment, $Y^a$ and $Y^b$ are both —$CH_2$— and W is $C_{6-10}$ arylene optionally substituted with 1 to 3 substituents independently selected from $R^b$ as defined herein; more preferably, W is phenylene. In another preferred embodiment, $Y^a$ and $Y^b$ are both —$CH_2CH_2$— and W is —O—.

When present, W is preferably $C_{6-10}$ arylene or —O—. More preferably, W is phenylene or —O—.

Preferably, $R^2$ is hydrogen or $C_{1-3}$ alkyl. More preferably, $R^2$ is hydrogen.

When present, each $R^3$ is preferably independently selected from $C_{1-6}$ alkyl, $C_{3-6}$ cycloalkyl, —$OR^d$, —$SR^d$, —F or —Cl; or two adjacent $R^3$ groups are joined to form $C_{3-6}$ alkylene.

In a preferred embodiment, $R^4$ is hydroxy and $R^5$ is hydrogen. In another preferred embodiment, $R^4$ is hydrogen and $R^5$ is hydroxy.

Preferably, $R^6$ is hydrogen and $R^7$ is methyl.

Preferably, $R^8$ is hydrogen.

Preferably, one of $X^1$ and $X^2$ is chloro and the other is hydrogen; or both are chloro. More preferably, $X^1$ and $X^2$ are both chloro.

In a preferred embodiment, $R^4$ is hydroxy; $R^5$ is hydrogen; $R^6$ is hydrogen; $R^7$ is methyl; $R^8$ is hydrogen; and $X^1$ and $X^2$ are both chloro (i.e., the glycopeptide portion is vancomycin).

In another preferred embodiment, $R^4$ is hydrogen; $R^5$ is hydroxy; $R^6$ is hydrogen; $R^7$ is methyl; $R^8$ is a group of formula (i); and $X^1$ and $X^2$ are both chloro (i.e., the glycopeptide portion is chloroorieniticin or A82846B).

In a preferred embodiment, m is 0. In another preferred embodiment, m is 1 or 2; more preferably, 1. In still another preferred embodiment, m is 2 and the two $R^3$ groups are joined to form a $C_{3-5}$ alkylene group; more preferably a $C_{3-4}$ alkylene group.

A preferred group of compounds of formula I are those of formula Ia wherein $R^1$ is —$Y^a$—$(W)_n$—$Y^b$—, where n is 0 and $Y^a$ and $Y^b$ are joined together to form a —$(CH_2)_{2-8}$— group; $R^2$ is hydrogen and m is 0; or a pharmaceutically-acceptable salt thereof. In this embodiment, $R^1$ (i.e., $Y^a$ and $Y^b$ taken together) is preferably a —$(CH_2)_2$—, —$(CH_2)_3$—, —$(CH_2)_4$—, —$(CH_2)_5$— or —$(CH_2)_6$— group; more preferably, —$(CH_2)_3$—.

Another preferred group of compounds of formula I are those of formula Ia wherein $R^1$, $R^2$, $R^3$ and m are as defined in Table I, or a pharmaceutically-acceptable salt thereof.

$R^1$ and $R^2$ are preferably as defined herein including any preferred embodiments, substituents or values Definitions When describing the compounds, compositions, methods and processes of this invention, the following terms have the following meanings, unless otherwise indicated.

The term "alkyl" refers to a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" refers to a divalent saturated hydrocarbon group which may be linear or branched. Unless otherwise defined, such alkylene groups typically contain from 1 to 10 carbon atoms. Representative alkylene groups

TABLE I

| Ex. No. | $R^1$ | | | | $R^2$ | $R^3$ | m |
|---|---|---|---|---|---|---|---|
| | $Y^a$ | W | $Y^b$ | n | | | |
| 1 | —$CH_2CH_2$— | — | —$CH_2$— | 0 | —H | — | 0 |
| 2 | —$CH_2CH_2$— | — | —$CH_2$— | 0 | —H | 2-$CH_3$— | 1 |
| 3 | —$CH_2CH_2$— | — | —$CH_2$— | 0 | —H | 3-$CH_3$— | 1 |
| 4 | —$CH_2CH_2$— | — | —$CH_2$— | 0 | —H | 4-$CH_3$— | 1 |
| 5 | —$CH_2CH_2$— | — | —$CH_2$— | 0 | —H | 2-$CH_3O$— | 1 |
| 6 | —$CH_2CH_2$— | — | —$CH_2$— | 0 | —H | 3-$CH_3O$— | 1 |
| 7 | —$CH_2CH_2$— | — | —$CH_2$— | 0 | —H | 4-$CH_3O$— | 1 |
| 8 | —$CH_2CH_2$— | — | —$CH_2$— | 0 | —H | 2-$CH_3S$— | 1 |
| 9 | —$CH_2CH_2$— | — | —$CH_2$— | 0 | —H | 3-$CH_3S$— | 1 |
| 10 | —$CH_2CH_2$— | — | —$CH_2$— | 0 | —H | 4-$CH_3S$— | 1 |
| 11 | —$CH_2CH_2$— | — | —$CH_2$— | 0 | —H | 2-F— | 1 |
| 12 | —$CH_2CH_2$— | — | —$CH_2$— | 0 | —H | 3-F— | 1 |
| 13 | —$CH_2CH_2$— | — | —$CH_2$— | 0 | —H | 4-F— | 1 |
| 14 | —$CH_2CH_2$— | — | —$CH_2$— | 0 | —H | 2-Cl— | 1 |
| 15 | —$CH_2CH_2$— | — | —$CH_2$— | 0 | —H | 3-Cl— | 1 |
| 16 | —$CH_2CH_2$— | — | —$CH_2$— | 0 | —H | 4-Cl— | 1 |
| 17 | —$CH_2CH_2$— | — | —$CH_2$— | 0 | —H | 2-Ph—[1] | 1 |
| 18 | —$CH_2CH_2$— | — | —$CH_2$— | 0 | —H | 3-Ph— | 1 |
| 19 | —$CH_2CH_2$— | — | —$CH_2$— | 0 | —H | 4-Ph— | 1 |
| 20 | —$CH_2CH_2$— | — | —$CH_2$— | 0 | —H | 4-cyclopropyl- | 1 |
| 21 | —$CH_2CH_2$— | — | —$CH_2$— | 0 | —H | 4-[HOOC$CH_2$S—] | 1 |
| 22 | —$CH_2CH_2$— | — | —$CH_2$— | 0 | —H | 4-$NH_2C(O)$— | 1 |
| 23 | —$CH_2CH_2$— | — | —$CH_2$— | 0 | —H | 2,3-di-$CH_3$— | 2 |
| 24 | —$CH_2CH_2$— | — | —$CH_2$— | 0 | —H | 3,4-di-$CH_3$— | 2 |
| 25 | —$CH_2CH_2$— | — | —$CH_2$— | 0 | —H | 3,5-di-$CH_3$— | 2 |
| 26 | —$CH_2CH_2$— | — | —$CH_2$— | 0 | —H | 3,4-di-$CH_3O$— | 2 |
| 27 | —$CH_2CH_2$— | — | —$CH_2$— | 0 | —H | 3-$CH_3$-4-$CH_3O$— | 2 |
| 28 | —$CH_2CH_2$— | — | —$CH_2$— | 0 | —H | 3-$CH_3O$-4-F— | 2 |
| 29 | —$CH_2CH_2$— | — | —$CH_2$— | 0 | —H | 2,3-[—$(CH_2)_4$—) | 2 |
| 30 | —$CH_2CH_2$— | — | —$CH_2$— | 0 | —H | 2,3-(—$CH_2CH_2CH_2$—) | 2 |
| 31 | —$(CH_2)_3$— | — | —$(CH_2)_3$— | 0 | —H | — | 0 |
| 32 | —$CH_2CH_2$— | —O— | —$CH_2CH_2$— | 1 | —H | — | 0 |
| 33 | —$CH_2$— | 1,4-(—Ph—)[2] | —$CH_2$— | 1 | —H | — | 0 |

[1]Ph = phenyl
[2]1,4-(—Ph—) = 1,4-phenylene

In the intermediate of formula H:

Q is preferably halo or the defined pyridinium group.

$P^1$ is preferably hydrogen or tert-butoxycarbonyl.

$P^2$ is preferably hydrogen or triphenylmethyl.

$P^3$ is preferably hydrogen or p-methoxybenzyl.

$R^1$, $R^2$, $R^3$ and m are preferably as defined herein including any preferred embodiments, substituents or values.

In the intermediate of formula II:

$P^1$ is preferably hydrogen or tert-butoxycarbonyl.

$P^2$ is preferably hydrogen, formyl or triphenylmethyl.

$P^4$ is preferably hydrogen $C_{1-4}$alkyl or p-methoxybenzyl.

include, by way of example, methylene, ethane-1,2-diyl ("ethylene"), propane-1,2-diyl, propane-1,3-diyl, butane-1,4-diyl, pentane-1,5-diyl and the like.

The term "alkenyl" refers to a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like.

The term "alkynyl" refers to a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like.

The term "aryl" refers to a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

The term "arylene" refers to a divalent aromatic hydrocarbon having a single ring (i.e., phenylene) or fused rings (i.e., naphthalenediyl). Unless otherwise defined, such arylene groups typically contain from 6 to 10 carbon ring atoms. Representative arylene groups include, by way of example, 1,2-phenylene, 1,3-phenylene, 1,4-phenylene, naphthalene-1,5-diyl, naphthalene-2,7-diyl, and the like.

The term "cycloalkyl" refers to a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like.

The term "cycloalkylene" refers to a divalent saturated carbocyclic hydrocarbon group. Unless otherwise defined, such cycloalkylene groups typically contain from 3 to 10 carbon atoms. Representative cycloalkylene groups include, by way of example, cyclopropane-1,2-diyl, cyclobutyl-1,2-diyl, cyclobutyl-1,3-diyl, cyclopentyl-1,2-diyl, cyclopentyl-1,3-diyl, cyclohexyl-1,2-diyl, cyclohexyl-1,3-diyl, cyclohexyl-1,4-diyl, and the like.

The term "halo" refers to fluoro, chloro, bromo and iodo.

The term "heteroaryl" refers to a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heteroarylene" refers to a divalent aromatic group having a single ring or two fused rings and containing at least one heteroatom (typically 1 to 3 heteroatoms) selected from nitrogen, oxygen or sulfur in the ring. Unless otherwise defined, such heteroarylene groups typically contain from 5 to 10 total ring atoms. Representative heteroarylene groups include, by way of example, divalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heterocyclyl" or "heterocyclic" refers to a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom.

The term "cephalosporin" is used herein in its art recognized manner to refer to a β-lactam ring system having the following general formula and numbering system:

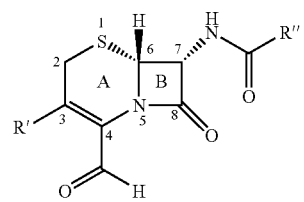

The term "glycopeptide antibiotic" or "glycopeptide" is used herein in its art recognized manner to refer to the class of antibiotics known as glycopeptides or dalbahpeptides. See, for example, R. Nagarajan, "Glycopeptide Anitibiotics", Marcel Dekker, Inc. (1994) and references cited therein. Representative glycopeptides include vancomycin, A82846A (eremomycin), A82846B (chloroorienticin A), A82846C, PA-42867-A-(orienticin A), PA-42867-C, PA-42867-D and the like.

The term "vancomycin" is used herein in its art recognized manner to refer to the glycopeptide antibiotic known as vancomycin. In the compounds of the present invention, the point of attachment for the linking moiety is at the "C-terminus" of vancomycin.

The term "pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids. Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like. Particularly preferred are citric, hydrobromic, hydrochloric, maleic, phosphoric, sulfuric and tartaric acids.

The term "salt thereof" refers to a compound formed when the hydrogen of an acid is replaced by a cation, such as a metal cation or an organic cation and the like (e.g., an $NH_4^+$ cation and the like). Preferably, the salt is a pharmaceutically-acceptable salt, although this is not required for salts of intermediate compounds which are not intended for administration to a patient.

The term "therapeutically effective amount" refers to an amount sufficient to effect treatment when administered to a patient in need of treatment.

The term "treating" or "treatment" as used herein refers to the treating or treatment of a disease or medical condition (such as a bacterial infection) in a patient, such as a mammal (particularly a human or a companion animal) which includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The term "growth-inhibiting amount" refers to an amount sufficient to inhibit the growth or reproduction of a microorganism or sufficient to cause death or lysis of the microorganism including gram-positive bacteria.

The term "cell wall biosynthesis-inhibiting amount" refers to an amount sufficient to inhibit cell wall biosynthesis in a microorganism including gram-positive bacteria.

The term "leaving group" refers to a functional group or atom which can be displaced by another functional group or atom in a substitution reaction, such as a nucleophilic substitution reaction. By way of example, representative leaving groups include chloro, bromo and iodo groups; and sulfonic ester groups, such as mesylate, tosylate, brosylate, nosylate and the like; activated ester groups, such as such as 7-azabenzotriazole-1-oxy and the like; acyloxy groups, such as acetoxy, trifluoroacetoxy and the like.

The term "protected derivatives thereof" refers to a derivative of the specified compound in which one or more functional groups of the compound are protected from undesired reactions with a protecting or blocking group. Functional groups which may be protected include, by way of example, carboxylic acid groups, amino groups, hydroxyl groups, thiol groups, carbonyl groups and the like. Representative protecting groups for carboxylic acids include esters (such as ap-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

The term "amino-protecting group" refers to a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like.

The term "carboxy-protecting group" refers to a protecting group suitable for preventing undesired reactions at an carboxy group. Representative carboxy-protecting groups include, but are not limited to, esters, such as methyl, ethyl, tert-butyl, benzyl (Bn), p-methoxybenzyl (PMB), 9-fluorenylmethyl (Fm), trimethylsilyl (TMS), tert-butyldimethylsilyl (TBS), diphenylmethyl (benzhydryl, DPM) and the like.

General Synthetic Procedures

The cross-linked glycopeptide-cephalosporin compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be readily determined by one skilled in the art by routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions for protection and deprotection of such functional groups are well known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Third Edition, Wiley, New York, 1999, and references cited therein.

In a preferred method of synthesis, the compounds of formula I are prepared by reacting a glycopeptide of formula 1:

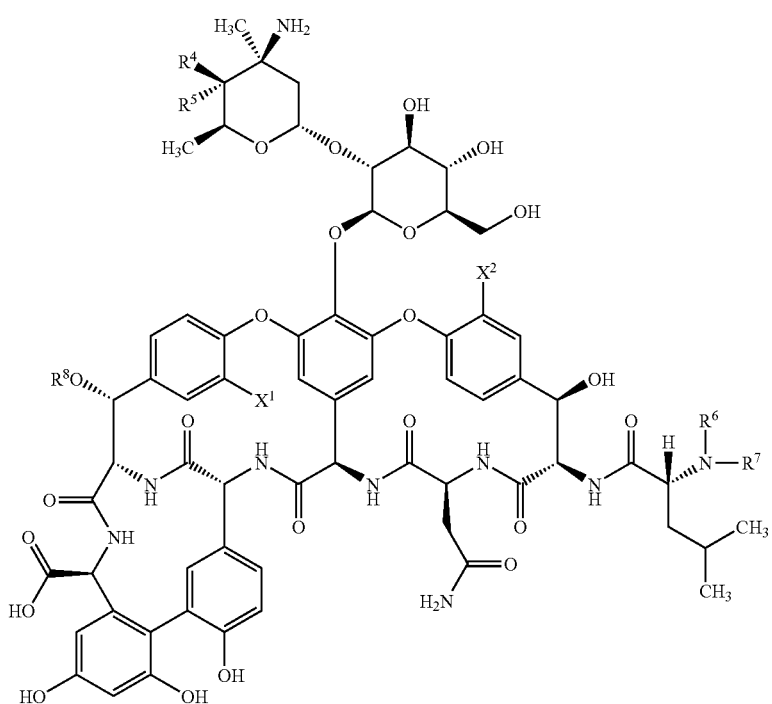

wherein $R^4$, $R^5$, $R^6$, $R^7$, $R^8$, $X^1$ and $X^2$ are as defined herein, or a salt thereof, with a compound of formula 2:

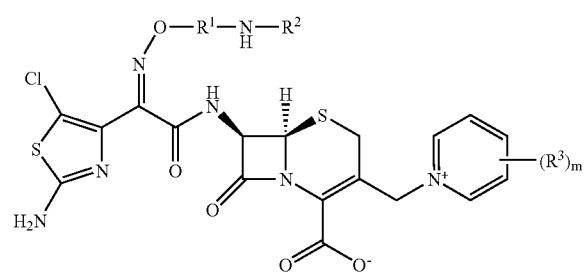

wherein $R^1$, $R^2$, $R^3$ and m are as defined herein, or a salt or protected derivative thereof, to provide a compound of formula I, or a salt or protected derivative thereof.

Typically, this reaction is conducted by coupling glycopeptide 1, or a salt thereof, with about 0.5 to about 1.5 equivalents, preferably about 0.9 to about 1.1 equivalents, of a compound of formula 2 in an inert diluent, such as DMF, using a conventional carboxylic acid-amine (peptide) coupling reagent. In this reaction, glycopeptide 1, or a salt thereof, is typically first contacted with the coupling reagent in the presence of an excess, preferably about 1.8 to about 2.2 equivalents, of an amine, such as diisopropylethylamine at a temperature ranging from about −20° C. to about 25° C., preferably at ambient temperature, for about 0.25 to about 3 hours. Preferably, excess trifluoroacetic acid (typically about 2 equivalents) is then added to form a TFA salt of any excess diisopropylethylamine. The reaction is then generally cooled to a temperature of about −20° C. to about 10° C., preferably to about 0° C., and intermediate 2 is added, followed by excess 2,4,6-collidine. This reaction is typically maintained at about 0° C. for about 1 to about 6 hours, or until the reaction is substantially complete.

A preferred coupling reagent for use in this reaction comprises about 0.5 to about 1.5 equivalents, preferably about 0.9 to about 1.1 equivalents, of benzotriazol-1-yloxytripyrrolidinophosphonium hexafluorophosphate (PyBOP) and about 0.5 to about 1.5 equivalents, preferably about 0.9 to about 1.1 equivalents, of 1-hydroxybenzotriazole (HOBT) or 1-hydroxy-7-azabenzotriazole (HOAT). Other suitable coupling reagents include O-(7-azabenzotriazol-1-yl)-N,N,N',N'-tetramethyluronium hexafluorophosphate (HATU); bis(2-oxo-3-oxazolidinyl)phosphinic chloride (BOP-Cl); diphenylphosphoryl azide (DPPA); diphenylphosphinic chloride; diphenyl chlorophosphate (DPCP) and HOAT; pentafluorophenyl diphenylphosphinate and the like.

After the coupling reaction is complete, any protecting groups present in the product are then removed using conventional procedures and reagents. Upon completion of this reaction, the reaction product, i.e., a compound of formula I, is isolated and purified using conventional procedures, such as column chromatography, HPLC, recrystallization and the like.

Glycopeptides of formula 1 suitable for use in the above procedure are either commercially available or they can be prepared by fermentation of the appropriate glycopeptide-producing organism, followed by isolation of the glycopeptide from the resulting fermentation broth using art recognized procedures and equipment.

The cephalosporin intermediate 2 used in the above procedure is readily prepared from commercially available starting materials and reagents using conventional proce dures. By way of example, intermediate 2 can be prepared as shown in Scheme A:

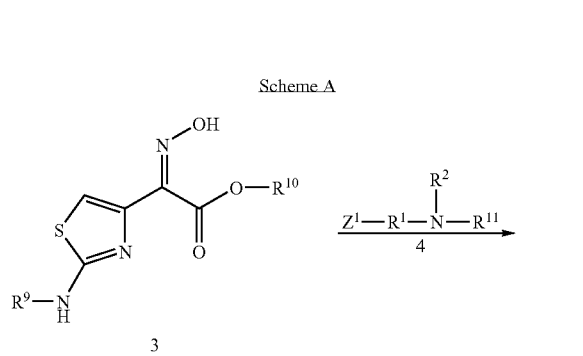

Scheme A

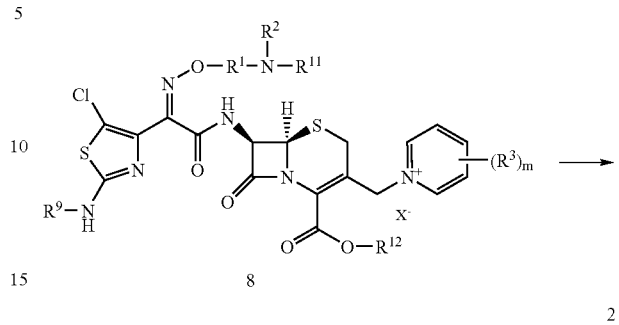

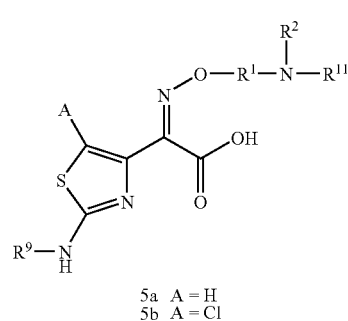

5a A = H
5b A = Cl

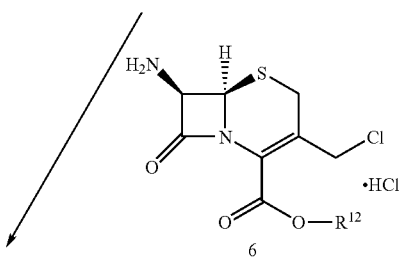

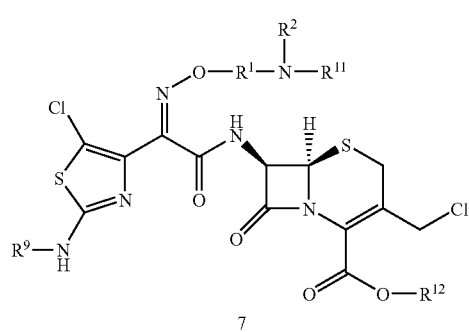

As illustrated in Scheme A, thiazole intermediate 3 (wherein $R^9$ is an amino-protecting group, such as a trityl group, and $R^{10}$ is a carboxy-protecting group, such as an ethyl group) is first reacted with an ω-functionalized amine of formula 4 (wherein $R^1$ and $R^2$ are as defined herein, $R^{11}$ is an amino-protecting group, such as a tert-butoxycarbonyl (BOC) group, and $Z^1$ is a leaving group, such as chloro, bromo, iodo, meslyate, tosylate and the like) to provide, after removal of the carboxy-protecting group (i.e., $R^{10}$), an intermediate of formula 5a.

This reaction is typically conducted by first contacting 3 with about 1.0 to about 1.1 equivalents, preferably with about 1.02 to about 1.06 equivalents, of a compound of formula 4 in an inert diluent, such as DMF, at a temperature ranging from about 0° C. to about 50° C., preferably at ambient temperature, for about 0.5 to about 6 hours, or until the reaction is substantially complete. This reaction is typically conducted in the presence of excess, preferably about 1.1 to about 5 equivalents, of a base, such as cesium carbonate. Additionally, when $Z^1$ is chloro or bromo, a catalytic amount, preferably about 0.2 to about 0.5 equivalents, of an trialkylammonium iodide, such as tetrabutylammonium iodide, is optionally added to facilitate the reaction by generating the iodo derivative of 4 in situ.

Removal of the carboxy-protecting group (i.e., $R^{10}$) then affords intermediate 5a. For example, when the carboxy-protecting group is an alkyl ester, such as an ethyl group, the ester is readily hydrolyzed to the carboxylic acid by contacting the ester with an excess, preferably with about 1.1 to about 2.5 equivalents, of an alkali metal hydroxide, such as sodium hydroxide or potassium hydroxide. This reaction is typically conducted in an inert diluent, such as ethanol, at a temperature ranging from about 0° C. to about 100° C. for about 0.5 to about 6 hours, or until the reaction is substantially complete, to afford intermediate 5a.

Thiazole compounds of formula 3 are commercially available from, for example, Aldrich, Milwaukee, Wis., or can be prepared from commercially available starting materials and reagents using conventional procedures.

Similarly, ω-functionalized amines of formula 4 are readily prepared from commercially-available starting materials and reagents using conventional procedures. Preferred compounds of formula 4 include, by way of illustration, N-BOC-3-bromopropylamine; N-BOC-6-iodohexylamine; N-BOC-2-(2-iodoethoxy)-ethylamine; N-BOC-4-(iodomethyl)benzylamine; and the like. These compounds are readily prepared from commercially available starting using well-known reagents and reaction conditions.

Intermediate 5a is then chlorinated to provide intermediate 5b. This reaction is typically conducted by contacting 5a with about 1.0 to about 1.2 equivalents, of a chlorinating agent, such as N-chlorosuccinimide, in an inert diluent, such as chloroform or DMF, at ambient temperature for about 6 to about 24 hours, or until the reaction is substantially complete.

5-Chloro-1,3-thiazole intermediate 5b is then coupled with intermediate 6 (wherein $R^{12}$ is hydrogen or a suitable carboxyl protecting group, such as a p-methoxybenzyl group) to provide intermediate 7. When $R^{12}$ is p-methoxybenzyl, intermediate 6 is commercially available from Otsuka, Japan. Typically, this reaction is conducted by contacting 5b with about 0.8 to about 1 equivalents of 6 in the presence of a coupling reagent under conventional coupling reaction conditions. A preferred coupling reagent for this reaction is phosphorous oxychloride (typically about 1.1 to about 1.2 equivalents) and an excess amount of an amine, such as 2,4,6-collidine or diisopropylethylamine. The coupling reaction is typically conducted in an inert diluent, such as THF, at a temperature ranging from about −50° C. to about 25° C. for about 0.5 to about 6 hours, or until the reaction is substantially complete, to afford intermediate 7. To avoid isomerization, this reaction is preferably conducted at −35° C. using 2,4,6-collidine as the base.

Intermediate 7 is then reacted with a pyridine or substituted pyridine to afford intermediate 8, where $R^3$ and n are as defined herein This reaction is typically conducted by first exchanging the chloro group in 7 with an iodo group by contacting 7 with about one equivalent of sodium iodide in acetone (Finkelstein reaction) or DMF at ambient temperature for about 0.25 to about 2 hours. The resulting iodo intermediate is typically not isolated, but is reacted in situ with about 1.1 to about 1.6 equivalents of a pyridine or substituted pyridine to afford 8. Typically, this reaction is conducted at ambient temperature for about 1 to about 12 hours, or until the reaction is substantially complete. The pyridine or substituted pyridines used in this reaction are either commercially available or can be prepared from commercially available starting materials and reagents using conventional procedures. Representative pyridine derivatives for use in this reaction include pyridine, 2-picoline, 3-picoline, 4-picoline, 2-methoxypyridine, 3-methoxypyridine, 4-methoxypyridine, 2-thiomethoxypyridine, 3-thiomethoxypyridine, 4-thiomethoxypyridine, 4-carboxythiomethoxypyridine, 2-fluoropyridine, 3-fluoropyridine, 4-fluoropyridine, 2-chloropyridine, 3-chloropyridine, 4-chloropyridine, 2-phenylpyridine, 3-phenylpyridine, 4-phenylpyridine, 4-cyclopropylpyridine, nicotinic acid, isonicotinic acid, nicotinamide, isonicotinamide, 2,3-lutidine, 3,4-lutidine, 3,5-lutidine, 3,4-dimethoxypyridine, 4-methoxy-3-methylpyridine, 4-fluoro-3-methoxypyridine, 2,3-cyclopentenopyridine, 2,3-cyclohexenopyridine and the like.

Alternatively, intermediate 5b can be coupled with a compound of formula 9:

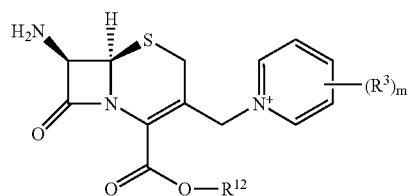

9 wherein $R^3$, $R^{12}$ and m are as defined herein, to afford intermediate 8. This reaction is typically conducted by contacting 5b with about 0.9 to about 1.1 equivalents of intermediate 9, or a salt thereof, in an inert diluent, such as DMF, in the presence of a coupling reagent, such as 1-(3-dimethylaminopropyl)-3-ethylcarbodiimide (EDC); PyBOP and HOAT or HOBT; HATU; BOP-Cl; DPPA; DPCP and HOAT; and the like. Generally, the coupling reaction is conducted at a temperature ranging from about −40° C. to about 25° C. for about 1 to about 12 hours, or until the reaction is substantially complete. Compounds of formula 9 are readily prepared from intermediate 6 by reaction of 6 with pyridine or a substituted pyridine under reaction conditions similar to those described above.

Removal of the protecting groups from intermediate 8 using conventional procedures and reagents then affords cephalosporin intermediate 2. For example, when $R^9$ is trityl, $R^{11}$ is tert-butoxycarbonyl and $R^{12}$ is para-methoxybenzyl, the protecting groups are conveniently removed by treating 8 with excess trifluoroacetic acid and excess anisole or triethylsilane in an inert diluent, such as dichloromethane or heptane, at ambient temperature for about 1 to about 12 hours, or until the reaction is complete. The resulting deprotected cephalosporin 2 is typically isolated and purified using conventional procedures, such as precipatation, lyophization and reverse-phase HPLC.

Alternatively, compounds of formula I can be prepared by reacting a glycopeptide derivative of formula 10:

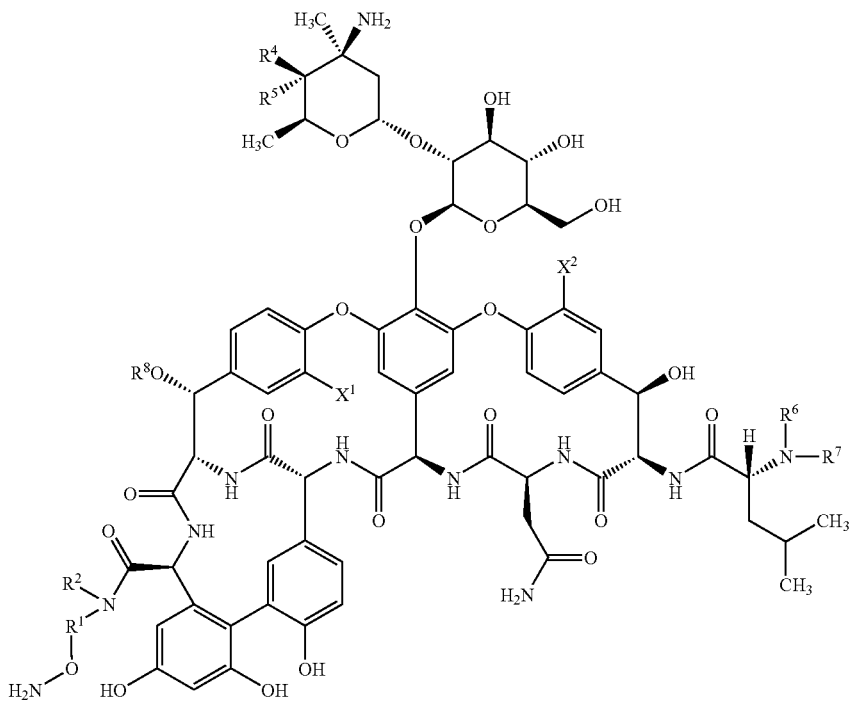

10 or a salt thereof, wherein $R^1$, $R^2$, $R^4$, $R^5$, $R^6$, $R^7$, $R^8$, $X^1$ and $X^2$ are as defined herein, with a cephalosporin derivative of formula 11:

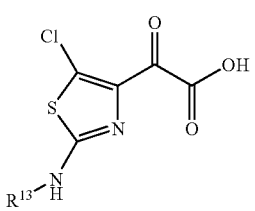

11 or a salt or protected derivative thereof (wherein $R^3$ and m are as defined herein) to afford a compound of formula I, or salt thereof.

This reaction is typically conducted by contacting 10 with about 1 to about 1.5 equivalents of 11 in an inert diluent, such as water, methanol or mixtures thereof, at a pH ranging from about 4 to about 6.5. This reaction is generally conducted at a temperature ranging from about −20° C. to about 40° C. for about 1 to about 6 hours, or until the reaction is substantially complete.

The vancomycin derivatives of formula 10 employed in this reaction are readily prepared by coupling vancomycin, or a salt thereof, with a phthalimido derivative of the formula:

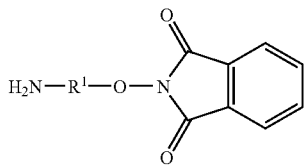

wherein $R^1$ is as defined herein, under conventional coupling conditions. For example, this reaction is typically conducted by contacting vancomycin with about 1.1 to about 1.2 equivalents of the phthalimido compound in the presence of a coupling reagent, such as PyBOP and HOAT and the like, and a suitable base, such as diisopropylethylamine. Generally, the reaction is conducted in an inert diluent, such as DMF, at a temperature ranging from about −20° C. to about 40° C. for about 0.5 to about 6 hours, or until the reaction is substantially complete. The phthalimido compounds employed in this reaction are readily prepared using conventional procedures and reagents.

Cephalosporin derivatives of formula 11 can be prepared, for example, by coupling a compound of formula 9 above with a thiazole compound of formula 12:

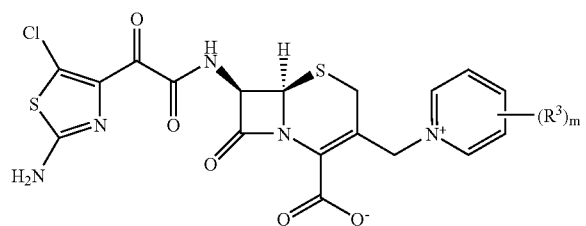

12 or a salt thereof, wherein $R^{13}$ is hydrogen or an amino-protecting group (such as a formyl or trityl group). This coupling reaction is typically conducted by contacting 9 with about 0.9 to about 1.1 equivalents of 12 in an inert diluent, such as DMF, in the presence of a coupling reagent, such as EDC and HOAT, and a suitable base, such as 2,4,6-collidine. Generally, this reaction is conducted at a temperature ranging from about −20° C. to about 20° C. for about 0.5 to about 6 hours, or until the reaction is substantially complete.

Additionally, compounds of formula I can be prepared by reacting a glycopeptide derivative of formula 13:

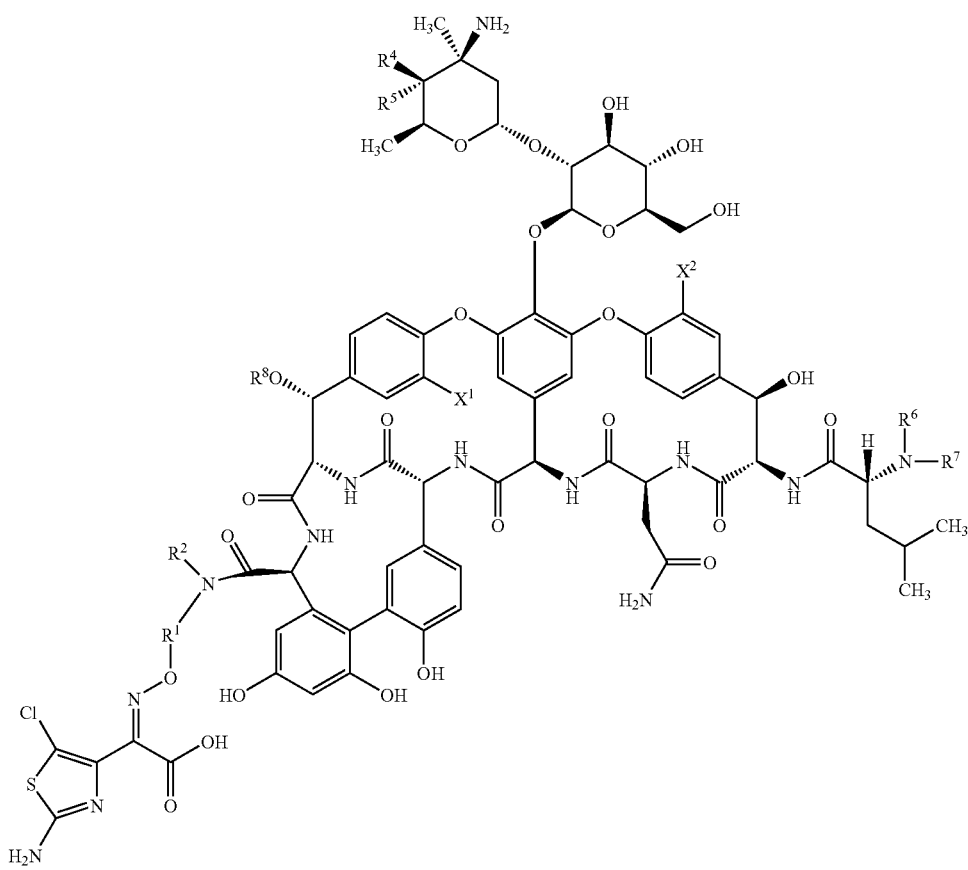

13 or a salt thereof, wherein $R^1$, $R^2$, $R^4$, $R^5$, $R^6$, $R^7$, $R^8$, $X^1$ and $X^2$ are as defined herein, with a compound of formula 9 above to afford a compound of formula I, or a salt thereof.

This coupling reaction is typically conducted by contacting 13 with a coupling reagent, such as DIPC and HOAT, and about 0.5 to about 2 equivalents of 9 in an inert diluent, such as DMF, in the presence of a suitable base, such as 2,4,6-collidine. Generally, this reaction is conducted at a temperature ranging from about −20° C. to about 40° C. for about 1 to about 6 hours, or until the reaction is substantially complete.

The compound of formula 13 used in this reaction is readily prepared by coupling vancomycin with intermediate 5b above, using conventional coupling procedures described herein.

Further details regarding specific reaction conditions and procedures for preparing representative compounds of this invention or intermediates thereto are described in the Examples set forth below.

Pharmaceutical Formulations

The cross-linked glycopeptide-cephalosporin compounds of this invention are typically administered to a patient in the form of a pharmaceutical composition. Accordingly, in one of its composition aspects, this invention is directed to a pharmaceutical composition comprising a pharmaceutically-acceptable carrier or excipient and a therapeutically effective amount of a compound of formula I or a pharmaceutically acceptable salt thereof.

Any conventional carrier or excipient may be used in the pharmaceutical compositions of this invention. The choice of a particular carrier or excipient, or combinations of carriers or exipients, will depend on the mode of administration being used to treat a particular patient or type of bacterial infection. In this regard, the preparation of a suitable pharmaceutical composition for a particular mode of administration, such as oral, topical, inhaled or parenteral administration, is well within the scope of those skilled in the pharmaceutical arts. Additionally, the ingredients for such compositions are commercially-available from, for example, Sigma, P.O. Box 14508, St. Louis, Mo. 63178. By way of further illustration, conventional formulation techniques are described in *Remington's Pharmaceutical Sciences*, Mace Publishing Co., Philadelphia, Pa. 17$^{th}$ Ed. (1985) and *"Modern Pharmaceutics,"* Marcel Dekker, Inc. 3$^{rd}$ Ed. (G. S. Banker & C. T. Rhodes, Eds.).

The pharmaceutical compositions of this invention will typically contain a therapeutically effective amount of a compound of formula I or a pharmaceutically-acceptable salt thereof. Typically, such pharmaceutical compositions will contain from about 0.1 to about 90% by weight of the active agent, and more generally from about 10 to about 30% of the active agent.

Preferred pharmaceutical compositions of this invention are those suitable for parenteral administration, particularly intravenous administration. Such pharmaceutical compositions typically comprise a sterile, physiologically-acceptable aqueous solution containing a therapeutically effective amount of a compound of formula I or a pharmaceutically-acceptable salt thereof.

Physiologically-acceptable aqueous carrier solutions suitable for intravenous administration of active agents are well-known in the art. Such aqueous solutions include, by way of example, 5% dextrose, Ringer's solutions (lactated Ringer's injection, lactated Ringer's plus 5% dextrose injection, acylated Ringer's injection), Normosol-M, Isolyte E, and the like.

Optionally, such aqueous solutions may contain a co-solvent, for example, polyethylene glycol; a chelating agent, for example, ethylenediamine tetracetic acid; a solubilizing agent, for example, a cyclodextrin; an anti-oxidant, for example, sodium metabisulphite; and the like.

If desired, the aqueous pharmaceutical compositions of this invention can be lyophilized and subsequently reconstituted with a suitable carrier prior to administration. In a preferred embodiment, the pharmaceutical composition is a lyophilized composition comprising a pharmaceutically-acceptable carrier and a therapeutically effective amount of a compound of formula I, or a pharmaceutically-acceptable salt thereof. Preferably, the carrier in this composition comprises sucrose, mannitol, dextrose, dextran, lactose or a combination thereof. More preferably, the carrier comprises sucrose, mannitol, or a combination thereof.

In one embodiment, the pharmaceutical compositions of this invention contain a cyclodextrin. When used in the pharmaceutical compositions of this invention, the cyclodextrin is preferably hydroxypropyl-$\beta$-cyclodextrin or sulfobutyl ether $\beta$-cyclodextrin. In such formulations, the cyclodextrin will comprise about 1 to 25 weight percent; preferably, about 2 to 10 weight percent of the formulation. Additionally, the weight ratio of cyclodextrin to active agent will typically range from about 1:1 to about 10:1.

The pharmaceutical compositions of this invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be packaged in sterile, hermetically-sealed ampoules and the like.

The following formulations illustrate representative pharmaceutical compositions of the present invention:

FORMULATION EXAMPLE A

A frozen solution suitable for preparing an injectable solution is prepared as follows:

| Ingredients | Amount |
|---|---|
| Active Compound | 10 to 1000 mg |
| Excipients (e.g., dextrose) | 0 to 50 g |
| Water for Injection Solution | 10 to 100 mL |

Representative Procedure: The excipients, if any, are dissolved in about 80% of the water for injection and the active compound is added and dissolved. The pH is adjusted with 1 M sodium hydroxide to 3 to 4.5 and the volume is then adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The vial is capped, labeled and stored frozen.

FORMULATION EXAMPLE B

A lyophilized powder suitable for preparing an injectable solution is prepared as follows:

| Ingredients | Amount |
|---|---|
| Active Compound | 10 to 1000 mg |
| Excipients (e.g., mannitol and/or sucrose) | 0 to 50 g |
| Buffer Agent (e.g., citrate) | 0 to 500 mg |
| Water for Injection | 10 to 100 mL |

Representative Procedure: The excipients and/or buffering agents, if any, are dissolved in about 60% of the water for injection. The active compound is added and dissolved and the pH is adjusted with 1 M sodium hydroxide to 3 to 4.5 and the volume is adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The formulation is then freeze-dried using an appropriate lyophilization cycle. The vial is capped (optionally under partial vacuum or dry nitrogen), labeled and stored under refrigeration.

FORMULATION EXAMPLE C

An injectable solution for intravenous administration to a patient is prepared from Formulation Example B above as follows:

Representative Procedure: The lyophilized powder of Formulation Example B (e.g., containing 10 to 1000 mg of active compound) is reconstituted with 20 mL of sterile water and the resulting solution is further diluted with 80 mL of sterile saline in a 100 mL infusion bag. The diluted solution is then administered to the patient intravenously over 30 to 120 minutes.

Utility

The cross-linked glycopeptide-cephalosporin compounds of the invention are useful as antibiotics. For example, the compounds of this invention are useful for treating or preventing bacterial infections and other bacteria-related medical conditions in mammals, including humans and their companion animals (i.e., dogs, cats, etc.) which are caused by microorganisms susceptible to the compounds of this invention.

Accordingly, in one of its method aspects, this invention provides a method of treating a bacterial infection in a mammal, the method comprising administering to a mammal in need of treatment, a pharmaceutical composition comprising a pharmaceutically-acceptable carrier and a therapeutically effective amount of a compound of formula I, or a pharmaceutically-acceptable salt thereof.

By way of illustration, the compounds of this invention are particularly useful for treating or preventing infections caused by Gram-positive bacteria and related microorganisms. For example, the compounds of this invention are effective for treating or preventing infections caused by certain *Enterococcus* spp.; *Staphylococcus* spp., including coagulase negative staphylococci (CNS); *Streptococcus* spp.; *Listeria* spp.; *Clostridium* ssp.; *Bacillus* spp.; and the like. Examples of bacterial species effectively treated with the compounds of this invention include, but are not limited to, methicillin-resistant *Staphylococcus aureus* (MRSA); methicillin-susceptible *Staphylococcus aureus* (MSSA); glycopeptide intertnediate-susceptible *Staphylococcus aureus* (GISA); methicillin-resistant *Staphylococcus epidermitis* (MRSE); methicillin-sensitive *Staphylococcus epidermitis* (MSSE); vancomycin-sensitive *Enterococcus faecalis* (EFSVS); vancomycin-sensitive *Enterococcus faecium* (EFMVS); penicillin-resistant *Streptococcus pneumoniae* (PRSP); *Streptococcus pyogenes*; and the like. Compounds of this invention are less effective or not effective for treating or preventing infections caused by strains of bacteria which are resistant to both vancomycin and cephalosporins.

Representative types of infections or bacteria-related medical conditions which can be treated or prevented with the compounds of this invention include, but are not limited to, skin and skin structure infections, urinary tract infections, pneumonia, endocarditis, catheter-related blood stream infections, osteomyelitis, and the like. In treating such conditions, the patient may already be infected with the microorganism to be treated or merely be susceptible to infection in which case the active agent is administered prophylactically.

The compounds of this invention are typically administered in a therapeutically effective amount by any acceptable route of administration. Preferably, the compounds are administered parenterally. The compounds may be administered in a single daily dose or in multiple doses per day. The treatment regimen may require administration over extended periods of time, for example, for several days or for one to six weeks or longer. The amount of active agent administered per dose or the total amount administered will typically be determined by the patient's physician and will depend on such factors as the nature and severity of the infection, the age and general health of the patient, the tolerance of the patient to the active agent, the microorganism(s) causing the infection, the route of administration and the like.

In general, suitable doses will range of from about 0.25 to about 10.0 mg/kg/day of active agent, preferably from about 0.5 to about 2 mg/kg/day. For an average 70 kg human, this would amount to about 15 to about 700 mg per day of active agent, or preferably about 35 to about 150 mg per day.

Additionally, the compounds of this invention are effective for inhibiting the growth of bacteria. In this embodiment, bacteria are contacted either in vitro or in vivo with a growth-inhibiting amount of a compound of formula I or pharmaceutically-acceptable salt thereof. Typically, a growth-inhibiting amount will range from about 0.008 µg/mL to about 50 µg/mL; preferably from about 0.008 µg/mL to about 25 µg/mL; and more preferably, from about 0.008 µg/mL to about 10 µg/mL. Inhibition of bacterial growth is typically evidenced by a decrease or lack of reproduction by the bacteria and/or by lysis of the bacteria, i.e., by a decrease in colony-forming units in a given volume (i.e., per mL) over a given period of time (i.e., per hour) compared to untreated bacteria.

The compounds of this invention are also effective for inhibiting cell wall biosynthesis in bacteria. In this embodiment, bacterial are contacted either in vitro or in vivo with a cell wall biosynthesis-inhibiting amount of a compound of formula I or pharmaceutically-acceptable salt thereof. Typically, a cell wall biosynthesis-inhibiting amount will range from about 0.04 µg/mL to about 50 µg/mL; preferably from about 0.04 µg/mL to about 25 µg/mL; and more preferably, from about 0.04 µg/mL to about 10 µg/mL. Inhibition of cell wall biosynthesis in bacteria is typically evidenced by inhibition or lack of growth of the bacteria including lysis of the bacteria.

In addition to surprising and unexpected antibacterial properties, compounds of this invention have also been found to possess acceptable mammalian safety and acceptable aqueous solubility. Additionally, compounds of this invention have been found to have surprising and unexpectedly rapid cidality against certain bacteria, including methicillin-resistant *Staphylococci aureus* (MRSA) and methicillin-resistant *Staphylococci epidermitis* (MRSE). These properties, as well as the antibiotic utility of the compounds of this invention, can be demonstrated using various in vitro and in vivo assays well-known to those skilled in the art. For example, representative assays are described in further detail in the following Examples.

EXAMPLES

The following synthetic and biological examples are offered to illustrate this invention and are not to be construed in any way as limiting the scope of this invention. In the examples below, the following abbreviations have the following meanings unless otherwise indicated. Abbreviations not defined below have their generally accepted meaning.

BOC=tert-butoxycarbonyl
CFU=colony-forming units
DCM=dichloromethane
DIPEA=diisopropylethylamine
DMF=N,N-dimethylformamide
DMSO=dimethyl sulfoxide
EtOAc=ethyl acetate
HOAT=1-hydroxy-7-azabenzotriazole
HPLC=high performance liquid chromatography
MIC=minimum inhibitory concentration
MS=mass spectrometry
PMB=p-methoxybenzyl
PyBOP=benzotriazol-1-yloxytripyrrolidino-phosphonium hexafluorophosphate
THF=tetrahydrofuran
TLC=thin layer chromatography
TFA=trifluoroacetic acid All temperatures reported in the following examples are in degrees Celsius (° C.) unless otherwise indicated. Also, unless noted otherwise, reagents, starting materials and solvents were purchased from commercial suppliers (such as Aldrich, Fluka, Sigma and the like) and were used without further purification. Vancomycin hydrochloride semi-hydrate was purchased from Alpharma, Inc., Fort Lee, N.J. 07024 (Alpharma AS, Oslo, Norway).

Reverse-phase HPLC was typically conducted using a $C_{18}$ column and (A) 98% water, 2% acetonitrile, 0.1% TFA, with an excessing gradient (e.g., 0 to about 70%) of (B) 10% water, 90% acetonitrile, 0.1% TFA, unless otherwise stated.

Example A

Synthesis of (7R)-7-[(Z)-2-(2-Amino-5-chlorothiazol-4-yl)-2-(3-aminopropoyimino)acetamido]-3-[(1-pyridinio)methyl]-3-cephem-4-carboxylate bis-Trifluoroacetic Acid Salt The following synthesis is illustrated, in part, in Scheme A above.

Step 1—Preparation of N-(tert-Butoxycarbonyl)-3-bromonropylamine (i.e. Compound 4 where $R^1$ is —$(CH_2)_3$—, $R^2$ is hydrogen, $R^{11}$ is BOC, and $Z^1$ is bromo)

3-Bromopropylamine hydrobromide (100 g, 457 mmol) was suspended in 1.6 L of anhydrous THF. This mixture was cooled to 0° C. in an ice/water bath and stirred vigorously while 190 mL of triethylamine was added. To this mixture was added dropwise tert-butoxycarbonyl anhydride (112.6 g, 516 mmol) in 200 mL THF. The ice bath was allowed to warm to ambient temperature and the mixture was stirred overnight at which time TLC indicated the reaction was complete. The mixture was then filtered and the filtrate was concentrated under vacuum. The residual oil was diluted with 1500 mL hexane and stored at −20° C. for 3 days. The mixture was then decanted and the residual solid was dried under vacuum to give 101 g (94% yield) of the title intermediate as a crystalline white solid.

$^1$H NMR (DMSO-$d_6$, 300 MHz): δ 1.35-1.39 (s, 9H), 1.91-1.95 (m, 2H), 2.99-3.04 (t, 2H), 3.43-3.52 (t, 2H), 6.95-6.99 (t, 1H).

Step 2—Preparation of Ethyl (Z)-2-(2-Triphenylmethylaminothiazol-4-yl)-2-(3-N-BOC-aminopropoxyimino)acetate (i.e. ethyl ester of Compound 5a where $R^1$ is —$(CH_2)_3$—, $R^2$ is hydrogen, $R^9$ is triphenylmethyl, $R^{11}$ is BOC, and A is hydrogen)

Ethyl (Z)-2-(2-triphenylmethylamino)thiazol-4-yl)-2-(hydroxyimino)acetate hydrochloride (100 g, 202.4 mmol) was dissolved in 700 mL of anhydrous DMF. To this stirred mixture was added cesium carbonate (230.8 g, 708.5 mmol) followed by tetrabutylammonium iodide (18.7 g, 50.6 mmol). N-BOC-3-bromopropylamine (50.6 g, 212.5 mmol) in DMF (100 mL) was then added dropwise over 30 minutes. The mixture was stirred for two hours at which time HPLC indicated that the reaction was complete. The mixture was then filtered and the filter cake was washed with 200 mL of DMF. The filtrate was dissolved in 2 L of ethyl acetate and washed with 700 mL of 1N HCl, followed by 700 mL of saturated aqueous sodium bicarbonate, and finally with 500 mL of brine. The organic layer was dried over sodium sulfate, filtered, and concentrated under vacuum. The residual oil was dissolved in 250 mL of boiling ethanol and poured into a beaker. Once the material had completely cooled, the residual clay-like solid was placed in a Büchner funnel and washed with 50 mL of ethanol previously cooled to −20° C. (NOTE: the product is moderately soluble in ethanol and use of larger amounts will decrease the overall yield of final product). After air-drying, the residual solid was ground into a fine powder in a mortar and pestle and dried under vacuum to give 117 g (94% yield) of the title intermediate as a fine off-white powder.

$^1$HNMR (DMSO-$d_6$, 300 MHz): δ 1.01-1.1 (t, 3H), 1.31 (s, 9H), 1.60-1.70 (t, 2H), 2.94-2.99 (m, 2H), 3.95-4.04 (m, 4H), 6.77-6.81 (t, 1H), 6.95 (s, 1H), 7.16-7.38 (m, 15H), 8.80 (s, 1H). MS m/z: 615.4 [M+H]$^+$.

Step 3—Preparation of (Z)-2-(2-Triphenylmethylaminothiazol-4-yl)-2-(3-N-BOC-aminopropoxyimino)acetate (i.e. Compound 5a where $R^1$ is —$(CH_2)_3$—, $R^2$ is hydrogen, $R^9$ is triphenylmethyl, $R^{11}$ is BOC, and A is hydrogen)

The ethyl ester from Step 2 above (84.2 g, 137 mmol) was suspended in 400 mL of anhydrous ethanol and heated in an oil bath to 80° C. with stirring. After all material had dissolved, potassium hydroxide (23.1 g, 411 mmol) in 150 mL of ethanol was added dropwise to the solution over 20 minutes. A precipitate began forming 10 minutes after addition of the base was complete, and within another 10 minutes the mixture was solid. The mixture was removed from the oil bath and cooled in an ice bath. Ethyl acetate and water were added to the cooled mixture which was then poured into a separatory funnel. The mixture was washed with 1N phosphoric acid, which caused the formation of a white solid (NOTE: washing the product with a stronger acid, such as 1N HCl causes degradation of the product). Water was added to the separatory funnel to dissolve this solid, and the organic layer was then washed with saturated aqueous sodium bicarbonate and with brine. The organic layer was dried over sodium sulfate, filtered and concentrated under vacuum to give the title intermediate (80 g, 99% yield) as a dark tan solid.

Step 4—Preparation of (Z)-2-(2-Triphenylmethylamino-5-chlorothiazol-4-yl)-2-(3-N-BOC-aminopropoxyimino)acetate (i.e. Compound 5b where $R^1$ is —$(CH_2)_3$—, $R^2$ is hydrogen, $R^9$ is triphenylmethyl, $R^{11}$ is BOC, and A is chloro)

The intermediate from Step 3 above (10 g, 17.04 mmol) was dissolved in 70 mL of chloroform and stirred while solid N-chlorosuccinimde (2.28 g, 17.04 mmol) was added (NOTE: experiments suggest that excess NCS may produce undesired side products). The mixture was stirred overnight (a minimum of 15 hours) at which time HPLC indicated that the reaction was complete. The mixture was then concentrated under vacuum and the residue was dissolved in a minimal amount of DMF. This mixture was added to vigorously stirred water to form a precipitate which was then collected by filtration. The solid was air-dried to give 9.5 g (90% yield) of the title intermediate as a tan solid. $^1$HNMR indicated only a minimal amount of succinimide remaining (NOTE: isolation of chlorinated product is not necessary for successful coupling in next step, but experiments suggest that residual succinimide may interfere with subsequent pyridine displacement). Alternatively, after the chlorination reaction was complete, the reaction mixture was washed with water (3×), brine, and then dried over anhydrous sodium sulfate. This solution was then filtered and concentrated under vacuum to give the title intermediate (90%) as a tan solid.

$^1$H NMR (DMSO-$d_6$, 300 MHz): δ 1.37 (s, 9H), 1.63-1.74 (t, 2H), 2.94-2.99 (m, 2H), 3.97-4.05 (t, 2H), 6.80-6.85 (t, 1H), 7.18-7.41 (m, 15H), 8.97 (s, 1H). MS m/z 621.3 [M+H]$^+$.

Step 5—Preparation of (7R)-7-[(Z)-2-(2-Triphenylmethylamino-5-chlorothiazol-4-yl)-2-(3-N-BOC-aminopropoxyimino)acetamido]-3-chloromethyl-3-cephem-4-carboxylate p-Methoxybenzyl Ester (i.e. Compound 7 where $R^1$ is —$(CH_2)_3$—, $R^2$ is hydrogen, $R^9$ is triphenylmethyl, $R^{11}$ is BOC, and $R^{12}$ is p-methoxybenzyl)

The intermediate from Step 4 (0.62 g, 1 mmol) was dissolved in 6 mL of anhydrous THF, and to this mixture was added 0.34 g (0.83 mmol) of 7-amino-3-chloromethylcephalosporanic acid p-methoxybenzyl ester hydrochloride (i.e, compound 6 where $R^{12}$ is PMB; obtained from Otsuka, Japan) in 4 mL of anhydrous THF. The resulting mixture was stirred under nitrogen and cooled to −35° C. To this cooled mixture was added diisopropylethylamine (0.52 mL, 3 mmol) followed by phosphorous oxychloride (0.11 mL, 1.2 mmol). This mixture was stirred at −20° C. for 30 minutes and then quenched with wet THF and diluted with ethyl acetate. This mixture was washed with water, 1N HCl, brine, dried over sodium sulfate, filtered and concentrated to give 0.88 g (100% yield) of the title intermediate as a brown-red solid. $^1$HNMR indicated no undesired isomerization and no residual succinimide.

$^1$H NMR (DMSO-$d_6$, 300 MHz): δ 1.37 (s, 9H), 1.63-1.74 (t, 2H), 2.94-2.99 (m, 2H), 3.4-3.74 (q, 2H), 3.75 (s, 3H), 3.97-4.05 (t, 2H), 4.40-4.59 (q, 2H), 5.11-5.25 (m, 3H), 5.49-5.54 (m, 1H), 6.75-6.81 (t, 1H), 6.90-6.96 (d, 2H), 7.18-7.41 (m, 17H), 8.97 (s, 1H), 9.41-9.44 (d, 1H). MS m/z 972.0 [M+H]$^+$.

(NOTE: Experiments suggest that DIPEA causes isomerization when the above reaction is carried out on larger scales. A modified procedure which uses 2,4,6-collidine as the base and which maintains the temperature at −35° C. for the entire course of the reaction—about 10 minutes—avoids this problem).

Step 6—Preparation of (7R)-7-[(Z)-2-(2-Triphenylmethylamino-5-chlorothiazol-4-yl)-2-(3-N-BOC-aminopropoxyimino)acetamido]-3-[(1-pyridinio)methyl]-3-cephem-4-carboxylate p-Methoxybenzyl Ester (i.e. Compound 8 where $R^1$ is —$(CH_2)_3$—, $R^2$ is hydrogen, $R^9$ is triphenylmethyl, $R^{11}$ is BOC, $R^{12}$ is p-methoxybenzyl and m is 0)

The intermediate from Step 5 (500 mg, 0.514 mmol) was dissolved in 2 mL of anhydrous acetone and protected from light using foil. The solution was stirred under a nitrogen atmosphere and 77 mg (0.514 mmol) of sodium iodide was added and the resulting mixture was stirred for 1 hour. Pyridine (63 μL, 0.772 mmol) was added and, after 90 minutes, the mixture was added to 25 mL of ethyl ether. This mixture was centrifuged and the resulting pellet was washed with ethyl ether and centrifuged again. The ether was decanted and the pellet was dried under vacuum to give a quantitative yield of the title intermediate as a tan solid which was used without further purification.

$^1$H NMR (DMSO-$d_6$, 300 MHz): δ=1.37 (s, 9H), 1.63-1.74 (t, 2H), 2.94-2.99 (m, 2H), 3.3-3.50 (q, 2H), 3.4-3.74 (q, 2H), 3.75 (s, 3H), 3.97-4.05 (t, 2H), 5.10-5.12 (d, 1H), 5.21 (s, 2H), 5.50-5.55 (m, 1H), 5.6 (s, 2H), 6.75-6.81 (t, 1H), 6.90-6.96 (d, 2H), 7.18-7.41 (m, 17H), 8.16-8.21 (t, 2H), 8.61-8.70 (t, 1H), 8.96 (s, 1H), 8.98-9.02 (d, 2H), 9.41-9.44 (d, 1H). MS m/z 1014.2 [M+H]$^+$.

Step 7—Preparation of (7R)-7-[(Z)-2-(2-Amino-5-chlorothiazol-4-yl)-2-(3-aminopropoxyimino)acetamido]-3-[(1-pyridinio)methyl]-3-cephem-4-carboxylate Bis-Trifluoroacetic Acid Salt (i.e. Compound 2 where $R^1$ is —$(CH_2)_3$—, $R^2$ is hydrogen and m is 0)

The intermediate from Step 6 (14.4 g) was dissolved in a 1:1 mixture of trifluoroacetic acid and dichloromethane (120 mL). To this stirring mixture was added 6.2 mL of anisole and the resulting mixture was stirred for 3 hours at room temperature. The mixture was then concentrated and the residue dissolved in ethyl acetate and extracted with water. The water layers were lyophilized and the resulting powder was dissolved in water and purified using reverse-phase prep HPLC. The resulting purified aqueous solution was then lyophilized to give 3.3 g (30% yield) of the title intermediate.

$^1$H NMR (DMSO-$d_6$, 300 MHz): δ=1.80-1.97 (t, 2H), 2.79-2.92 (m, 2H), 3.29-3.57 (q, 2H), 4.02-4.15 (t, 2H), 5.15-5.19 (d, 1H), 5.41-5.63 (q, 2H), 5.83-5.92 (m, 1H), 7.39 (s, 2H), 7.77 (s, 3H), 8.17-8.22 (t, 2H), 8.60-8.70 (t, 1H), 9.0-9.08 (d, 2H), 9.59-9.62 (d, 1H). MS m/z 553.1 [M+H]$^+$.

(NOTE: The above reaction can also be conducted using triethylsilane in place of the anisole. Additionally, the product can be isolated using ethyl ether trituration).

Example B

Synthesis of (7R)-7-[(Z)-2-(2-Amino-5-chlorothiazol-4-yl)-2-(3-aminopropoxyimino)acetamido]-3-[(2,3-cyclopenteno-1-pyridinio)methyl]-3-cephem-4-carboxylate bis-Trifluoroacetic Acid Salt Using the procedure described in Example A and substituting 2,3-cyclopentenopyridine (obtained from Koei, Japan) for pyridine in Step 6, the title intermediate was obtained.

$^1$H NMR (DMSO-$d_6$, 300 MHz): δ=1.82-1.947 (t, 2H), 2.18-2.29 (m, 2H), 2.40-2.58 (m, 2H), 2.81-2.95 (m, 2H), 3.09-3.17 (t, 2H), 3.21-3.30 (t, 2H), 4.10-4.19 (t, 2H), 5.15-5.19 (d, 1H), 5.40-5.61 (q, 2H), 5.83-5.92 (m, 1H), 7.39 (s, 2H), 7.77 (s, 3H), 7.89-7.96 (t, 2H), 8.42-8.48 (d, 1H), 8.62-8.69 (d, 1H), 9.60-9.63 (d, 1H). MS m/z 592.5 [M+H]$^+$.

Example C

Synthesis of (7R)-7-[(Z)-2-(2-Amino-5-chlorothiazol-4-yl)-2-(6-aminohexoxyimino)acetamido]-3-[(1-pyridinio)methyl]-3-cephem-4-carboxylate bis-Trifluoroacetic Acid Salt Using the procedure described in Example A and substituting N-BOC-6-iodohexylamine for N-BOC-3-bromopropylamine in Step 2 (and eliminating the tetrabutylammonium iodide), the title intermediate was obtained.

$^1$H NMR (DMSO-$d_6$, 300 MHz): δ 1.2 ppm (bs, 4H), 1.3 ppm (m, 2H), 1.5 ppm (m, 2H), 2.7 ppm (m, 2H), 3.3 ppm (dd, 2H), 4.0 ppm (t, 3H), 5.1 ppm (d, 1H), 5.5 ppm (dd, 2H), 5.8 ppm (dd, 1H), 7.25 ppm (bs, 2H), 7.6 ppm (bs, 3H), 8.2 ppm (dd, 2H), 8.6 ppm (dd, 1H), 9 ppm (dd, 2H), 9.5 ppm (d, 1H). MS m/z 594.3 (M+).

Example D

Synthesis of (7R)-7-[(Z)-2-(2-Amino-5-chlorothiazol-4-yl)-2-(2-(2-aminoethoxy)ethoxyimino)acetamido]-3-[(1-pyridinio)methyl]-3-cephem-4-carboxylate bis-Trifluoroacetic Acid Salt The procedure of Example A was used, except that the following procedure was substituted for Step 2:

Step 2—Preparation of Ethyl (Z)-2-(2-Triphenylmethylaminothiazol-4-yl)-2-[2-(2-N-BOC-aminoethyl)ethoxyimino]acetate (i.e. ethyl ester of Compound 5a where $R^1$ is —$(CH_2)_2$—O—$(CH_2)_2$—, $R^2$ is hydrogen, $R^9$ is triphenylmethyl, $R^{11}$ is BOC, and A is hydrogen)

The intermediate from Step 1 in Example A (42.5 g, 86 mmol) was added to a stirred suspension of N-BOC-2-(2-iodoethoxy)-ethylamine (28.5 g, 90 mmol) (prepared in three steps from 2-(2-hydroxyethoxy)ethanol, i.e., (i) $BOC_2O$, KOH, (ii) MsCl, $Et_3N$ and (iii) NaI) and cesium carbonate (84.1 g, 258 mmol) in DMF (300 mL). The suspension was stirred for 16 h at room temperature at which time HPLC indicated that the reaction was complete. The reaction mixture was then filtered and the filter cake washed with DMF (100 mL). The filtrate was diluted with ethyl acetate (1 L) and washed with water (300 mL), 1N HCl (200 mL), saturated aqueous sodium bicarbonate (200 mL) and brine (200 mL). The organic layer was dried over magnesium sulfate, filtered, and concentrated in vacuo. The residue was purified by flash column chromatography (ethyl acetate: hexane, 1:1) to afford 49.7 g (90% yield) of the title intermediate as an off-white solid.

$^1$H NMR (DMSO-d$_6$, 300 MHz): δ=2.96 (s, broad, 2H), 3.20-3.55 (q, 2H), 3.59 (t, 2H), 3.70 (t, 2H), 4.19 (t, 2H), 5.13 (d, 1H), 5.31-5.64 (q, 2H), 5.80 (dd, 1H), 7.40 (s, 2H), 7.87 (s, broad, 3H), 8.20 (t, 2H), 8.64 (t, 1H), 9.23 (d, 2H), 9.55 (d, 1H). MS m/z 503.1 [M-pyridine]$^+$.

Example E

Synthesis of (7R-7-[(Z)-2-(2-Amino-5-chlorothiazol-4-yl)-2-(4-aminomethylbenzyloxyimino)acetamido]-3-[(1-pyridinio)methyl]-3-cephem-4-carboxylate bis-Trifluoroacetic Acid Salt Using the procedure described in Example A and Step 2 of Example D and substituting N-BOC-4-(iodomethyl)benylamine (prepared in four step from 4-(aminomethyl)benzoic acid, i.e., (i) BOC$_2$O, KOH, (ii) LiAlH$_4$, (iii) MsCl, Et$_3$N and (iv) NaI) for N-BOC-2-(2-iodoethoxy)-ethylamine 3-bromopropylamine hydrobromide in Step 2, the title intermediate was obtained.

$^1$H NMR (DMSO-d$_6$, 300 MHz): δ=3.18-3.59 (q, 2H), 4.00 (s, broad, 2H), 5.13 (s, 2H), 5.15 (d, 2H), 5.40-5.64 (q, 2H), 5.85 (dd, 1H), 7.38-7.43 (m, 6H), 8.19-8.23 (m, 4H), 8.64 (t, 1H), 9.17 (d, 2H), 9.71 (d, 1H). MS m/z 614.1 [M+H]$^+$, 535.1 [M-pyridine]$^+$.

Example F (Comparative)

Synthesis of (7R)-7-[(Z)-2-(2-Aminothiazol-4-yl)-2-(3-aminopropoxyimino)acetamido]-3-[(1-pyridinio)methyl]-3-cephem-4-carboxylate bis-Trifluoroacetic Acid Salt By eliminating Step 4 in Example A above, the des-chloro derivative of the intermediate of Example A was prepared.

$^1$H NMR (DMSO-d$_6$, 300 MHz): δ=1.75-1.82 (t, 2H), 2.67-2.82 (m, 2H), 3.25-3.61 (q, 2H), 3.98-4.09 (t, 2H), 5.13-5.17 (d, 1H), 5.38-5.58 (q, 2H), 5.79-5.85 (m, 1H), 6.62 (s, 1H) 7.15-7.25 (s, broad, 2H), 7.60-7.75 (s, broad, 3H), 8.16-8.19 (t, 2H), 8.58-8.63 (t, 1H), 8.95-9.01 (d, 2H), 9.57-9.60 (d, 1H). MS m/z 518.6 [M+H]$^+$.

Example G

Synthesis of Vancomycin 3-(Aminooxy)propyl Amide

Step 1—Preparation of N-(3-Aminopropoxy)phthalimide

N-(tert-Butoxycarbonyl)-3-bromopropylamine (from Step 1 in Example A above) (9.58 g, 40.23 mmol) and N-hydroxypthalimide (6.36 g, 39 mmol) were dissolved in 70 mL of anhydrous DMF. To this solution was added diisopropylethylamine (7.01 mL, 40.23 mmol) resulting in a deep red color. The reaction was stirred at room temperature for 16 hours after which time, the reaction mixture was poured into 500 mL of diethyl ether. The resulting white precipitate was filtered off and discarded. The organic solution was washed with 2×200 mL saturated sodium bicarbonate and with 2×200 mL of water. The organic solution was dried over anhydrous magnesium sulfate, filtered and concentrated to give a white solid. This solid was then dissolved in 50 mL of DCM and 50 mL of TFA. After stirring for 1 hour, this solution was poured into 300 mL of diethyl ether. The resulting precipitate was filtered, washed with diethyl ether and dried under vacuum to afford the title intermediate as its trifluoroacetic acid salt.

$^1$H NMR (DMSO-d$_6$, 300 MHz): δ=1.90 (2H, qn), 2.95 (2H, t), 4.18 (2H, t), 7.79 (4H, s), 7.92 (3H, broad s).

Step 2—Preparation of Vancomycin 3-(Phthalimidooxy) propyl Amide

Vancomycin hydrochloride (10.0 g, 6.74 mmol) and the intermediate from Step 1 (2.70 g, 8.09 mmol) were slurried in 100 mL of anhydrous DMF. Diisopropylethylamine (4.70 mL, 26.98 mmol) was added and the resulting mixture was stirred at room temperature for 10 min. A solution of PyBOP (5.61 g, 10.78 mmol) and HOAt (1.65 g, 10.78 mmol) in DMF (20 mL) was then added, and the reaction was stirred at room temperature. After 1 hour, the reaction mixture was added to diethyl ether (500 mL). The resulting precipitate was filtered, washed with diethyl ether and dried under vacuum to yield the title intermediate as an off-white solid.

MS m/z=1651.8 (M+H)$^+$.

Step 3—Preparation of Vancomycin 3-(Aminooxy)propyl Amide

The intermediate from Step 2 (11.2 g, 6.74 mmol) was slurried in 80 mL of anhydrous DMF and hydrazine monohydrate (0.65 mL, 13.48 mmol) was added. The reaction was stirred at room temperature for 4.5 hours and then 1 mL of trifluoroacetic acid was added to the reaction mixture, followed by 300 mL of diethyl ether. After vigorous stirring, the resulting precipitate was filtered, washed with diethyl ether and dried under vacuum. The title compound was purified by reverse phase HPLC using a water/methanol gradient to afford the title intermediate as a lyophilized powder.

MS m/z=1522.9 (M+H)$^+$.

Example H

Synthesis of (7R)-7-[2-(2-Amino-5-chlorothiazol-4-yl)-2-oxoacetamido]-3-(1-pyridinio)methyl-3-cephem-4-carboxylate Bis-Trifluoroacetate Step 1—Preparation of Ethyl 2-(2-Formylamino-5-chlorothiazol-4-yl)-2-oxoacetate Ethyl 2-(Formylaminothiazol-4-yl)-2-oxoacetate (9.1 g, 39.87 mmol) (obtained from Aldrich, Milwaukee, Wis.) was slurried in 50 mL of anhydrous DMF. N-Chlorosuccinimide (5.6 g, 41.86 mmol) was added as a solid and the suspension was stirred at room temperature. After 18 hours, the reaction mixture was poured into 500 mL of water. The resulting white precipitate was filtered, washed with water and air dried to afford the title intermediate as a white solid.

$^1$H NMR (DMSO-d$_6$, 300 MHz): δ=1.2 (t, 3H), 4.3 (q, 2H), 8.55 (s, 1H).

Step 2—Preparation of 2-(2-Formylamino-5-chlorothiazol-4-yl)-2-oxoacetic Acid

To the intermediate from Step 1 (3.6 g, 13.7 mmol) was added 1M NaOH (30 mL, 30 mmol). The resulting suspension was stirred at room temperature for 2 hours (at which time the solution was clear) and 1M HCl (30 mL, 30 mmol) was then added, followed by 100 mL of water. After vigorous stirring, the resulting precipitate was filtered, washed with a minimum amount of cold water and air dried to afford the title intermediate as an off-white solid.

$^1$H NMR (DMSO-d$_6$, 300 MHz): δ=8.5 (s, 1H).

Step 3—Preparation of (7R)-7-[2-(2-Formylamino-5-chlorothiazol-4-yl)-2-oxoacetamido]-3-chloromethyl-3-cephem-4-carboxylate p-Methoxybenzyl Ester The intermediate from Step 2 (1.03 g, 4.37 mmol), 7-amino-3-chloromethylcephalosporanic acid p-methoxybenzyl ester hydrochloride (1.95 g, 4.81 mmol) and HOAt (0.74 g, 4.81 mmol) were slurried in 15 mL of anhydrous DMF. The reaction vessel was purged with nitrogen and then cooled to 0° C. with an external ice bath. 1-(3-Dimethylaminopropyl)-3-ethylcarbodiimide hydrochloride (0.92 g, 4.81 mmol) was added to the cold reaction mixture, followed by 2,4,6-collidine (0.64 mL, 4.81 mmol). The reaction was stirred at 0° C. for 2 hours and then poured into 200 mL of 0.5M HCl. The resulting precipitate was filtered, washed with water and air dried to afford the title intermediate as a red solid. The compound was used without further purification.

MS m/z=607 (M+Na)$^+$.

Step 4—Preparation of (7R)-7-[2-(2-Formylamino-5-chlorothiazol-4-yl)-2-oxoacetamido]-3-(1-pyridinio)methyl-3-cephem-4-carboxylate p-Methoxybenzyl Ester The intermediate from Step 3 (2.5 g, 4.27 mmol) and sodium iodide (0.64 g, 4.27 mmol) were dissolved in acetone and shielded from light by foil. The reaction was stirred for 10 minutes and then pyridine (0.42 mL, 5.12 mmol) was added. The reaction was then stirred at room temperature for 1 hour and then 300 mL of water were added. The resulting precipitate was filtered, washed with water and air-dried to provide a red solid. This solid was purified on reverse-phase HPLC and the resulting aqueous solution was lyophilized to afford the title intermediate as a lyophilized powder.

MS m/z=628.1 (M)$^+$.

Step 5—Preparation of (7R)-7-[2-(2-Amino-5-chlorothiazol-4-yl)-2-oxoacetamido]-3-(1-pyridinio)methyl-3-cephem-4-carboxylate Bis-Trifluoroacetate The intermediate from Step 4 (0.11 g, 0.18 mmol) was dissolved in 5 mL of methanol and concentrated aqueous hydrochloric acid (0.5 mL) was added. The resulting solution was stirred at room temperature for 1.5 hours. The methanol was removed under vacuum and acetonitrile (10 mL) was added. The solution was then concentrated in vacuum and to the residue as added DCM (2 mL) and TFA (2 mL) and the resulting mixture was stirred at room temperature for 1.5 hours. Diethyl ether (50 mL) was then added and the title intermediate was isolated by centrifugation. This intermediate was used without further purification.

MS m/z=479.9 (M)$^+$.

Example 1

Synthesis of Compound 13 where $R^1$ is
—(CH$_2$)$_3$—, $R^2$, $R^5$, $R^6$, $R^8$ are Hydrogen, $R^4$ is
Hydroxy, $R^7$ is Methyl, $X^1$ and $X^2$ are Chloro, and
m is 0

Step 1—Preparation of (Z)-2-(2-Amino-5-chlorothiazol-4-yl)-2-(3-aminopropoxyimino)acetate The intermediate from Step 4 in Example A (0.75 g, 1.21 mmol) was dissolved in 5 mL of DCM and 5 mL of trifluoroacetic acid. After 1 hour stirring at room temperature, 100 mL of diethyl ether was added. The resulting precipitate was filtered, washed with diethyl ether and dried under vacuum to afford the title intermediate as a brown solid Step 2—Preparation of Compound 13 where $R^1$ is
—(CH$_2$)$_3$—, $R^2$, $R^5$, $R^6$, $R^8$ are Hydrogen, $R^4$ is Hydroxy, $R^7$ is Methyl, $X^1$ and $X^2$ are Chloro, and m is 0

Vancomycin hydrochloride (1.3 g, 0.88 mmol) and HOAt (0.14 g, 0.088 mmol) were slurried in 3.5 mL of anhydrous DMSO. A solution of PyBOP (0.46 g, 0.88 mmol) in 3.5 mL of anhydrous DMF was added, followed by DIPEA (154 uL, 0.88 mmol). After stirring for 20 minutes, a solution of the intermediate from Step 1 (0.22 g, 0.44 mmol) in 1 mL of DMF was added, followed quickly by addition of DIEA (0.54 mL, 3.08 mmol). The reaction mixture was stirred at room temperature for 1 hour, then 0.5 mL of trifluoroacetic acid was added, followed quickly by the addition of 100 mL of Et$_2$O. The resulting precipitate was filtered, washed with Et$_2$O and dried in vacuum. The crude product was purified by reverse-phase-HPLC and the resulting aqueous solution was lyophilized to afford the title intermediate as a lyophilized powder.

MS m/z=1711.0 (M+H)$^+$.

Example 1

Synthesis of a Compound of Formula I where $R^1$ is
—(CH$_2$)$_3$—, $R^2$, $R^5$, $R^6$, $R^8$ are Hydrogen, $R^4$ is
Hydroxy, $R^7$ is Methyl, $X^1$ and $X^2$ are Chloro, and
m is 0 (Compound 1 in Table I)

Vancomycin hydrochloride (4.2 g, 2.8 mmol) was dissolved in 40 mL of DMSO. To this solution was added a solution of PyBOP (1.3 g, 2.6 mmol) and HOAT (0.35 g, 2.6 mmol) in 40 mL of DMF, followed by 0.98 mL (5.68 mmol) of diisopropylethylamine. This mixture was stirred at room temperature for 30 minutes and then quenched with 0.44 mL (5.7 mmol) of trifluoroacetic acid. The mixture was then cooled to 0° C. and a solution of the intermediate from Example A above (1.3 g, 2.6 mmol) in 20 mL of DMF at 0° C. was added, followed by 1.5 mL (11.4 mmol) of 2,4,6-collidine. The mixture was maintained at 0° C. for four hours and then quenched with 1.1 mL of trifluoroacetic acid. This mixture was then added to ethyl ether to form a precipitate, centrifuged, washed with ether, decanted and dried under vacuum. The resulting powder was dissolved in water and purified using prep HPLC. The fractions containing the desired product were lyophilized to give the tri-trifluoroacetic acid salt of the title compound. The anion of the salt was then exchanged using Amberlyte resin to afford the tri-hydrochloride salt of the title compound (1.4 g, 27% yield) as a white powder.

MS m/z 953.3 [[M+H]$^+$-pyridine]/2; 992.0 [M+H]$^+$/2.

Additionally, Compounds 2-30 shown in Table I are or were prepared using the procedures of Example A and Example 1 by using in place of the pyridine in Step 6 of Example A, the following substituted pyridines:

Example 2

2-Picoline

Example 3

3-Picoline

Example 4

4-Picoline

Example 5

2-Methoxypyridine

Example 6

3-Methoxypyridine

Example 7

4-Methoxypyridine

Example 8

2-Thiomethoxypyridine

Example 9
3-Thiomethoxypyridine

Example 10
4-Thiomethoxypyridine

Example 11
2-Fluoropyridine

Example 12
3-Fluoropyridine

Example 13
4-Fluoropyridine

Example 14
2-Chloropyridine

Example 15
3-Chloropyridine

Example 16
4-Chloropyridine

Example 17
2-Phenylpyridine

Example 18
3-Phenylpyridine

Example 19
4-Phenylpyridine

Example 20
4-Cyclopropylpyridine

Example 21
4-(Carboxythiomethoxy)pyridine

Example 22
Isonicotinamide

Example 23
2,3-Lutidine

Example 24
3,4-Lutidine

Example 25
3,5-Lutidine

Example 26
3,4-Dimethoxypyridine

Example 27
4-Methoxy-3-methylpyridine

Example 28
4-Fluoro-3-methoxypyridine

Example 29
2,3-Cyclohexenopyridine

Example 30
2,3-Cyclopentenopyridine

The above substituted pyridines are either commercially available or can be prepared by literature procedures.

Example 31

Synthesis of a Compound of Formula I where $R^1$ is —$(CH_2)_6$—, $R^2$, $R^5$, $R^6$, $R^8$ are Hydrogen, $R^4$ is Hydroxy, $R^7$ is Methyl, $X^1$ and $X^2$ are Chloro, and m is 0 (Compound 31 in Table I)

Using the procedure of Example 1 and substituting the intermediate of Example C for the intermediate of Example A, the title compound was prepared.
MS m/z 2026.5 (M+).

Example 32

Synthesis of a Compound of Formula I where $R^1$ is —$(CH_2)_2$—O—$(CH_2)_2$—, $R^2$, $R^5$, $R^6$, $R^8$ are Hydrogen, $R^4$ is Hydroxy, $R_7$ is Methyl, $X^1$ and $X^2$ are Chloro, and m is 0 (Compound 32 in Table I)

Using the procedure of Example 1 and substituting the intermediate of Example D for the intermediate of Example A, the title compound was prepared.
MS m/z 967.9 [(M-pyridine)/2]$^+$.

Example 33

Synthesis of a Compound of Formula I where $R^1$ is —$CH_2$-1,4-Ph—$CH_2$—, $R^2$, $R^5$, $R^6$, $R^8$ are Hydrogen, $R^4$ is Hydroxy, $R^7$ is Methyl, $X^1$ and $X^2$ are Chloro, and m is 0 (Compound 33 in Table I)

Using the procedure of Example I and substituting the intermediate of Example E for the intermediate of Example A, the title compound was prepared.
MS m/z 1967.0 [M+H]$^+$, 984.2 [(M-pyridine)/2]$^+$.

Example 34 (Comparative)

Synthesis of a des-Chloro Compound of Formula I where $R^1$ is —$(CH_2)_3$—, $R^2$, $R^5$, $R^6$, $R^8$ are Hydrogen, $R^4$ is Hydroxy, $R^7$ is Methyl, $X^1$ and $X^2$ are Chloro, and m is 0 (Compound 34)

Using the procedure of Example 1 and substituting the des-chloro cephalosporin intermediate of Example F for the intermediate of Example A, the title compound was prepared.

MS m/z 935.3 [[M+H]$^+$-pyridine]/2; 974.9 [M+H]$^+$/2.

Example 35

Determination of Minimal Inhibitory Concentrations (MICs)

Minimal inhibitory concentration (MICs) assays were performed using the broth microdilution method set forth in NCCLS guidelines (see, NCCLS. 2000. *Methods for Dilution Antimicrobial Susceptibility Tests for Bacteria That Grow Aerobically*; Approved Standard—Fifth Ed., Vol. 20, No. 2). Bacterial strains were obtained from the American Type Tissue Culture Collection (ATCC), Stanford University Hospital (SU), Kaiser Permanente Regional Laboratory in Berkeley (KPB), Massachusetts General Hospital (MGH), the Centers for Disease Control (CDC), the San Francisco Veterans' Administration Hospital (SFVA) or the University of California San Francisco Hospital (UCSF). Vancomycin-resistant enterococci were phenotyped as Van A or Van B based on their sensitivity to teicoplanin. Some vancomycin-resistant enterococci that had been genotyped as Van A, Van B, Van C1 or Van C2 were also obtained from the Mayo Clinic.

In this assay, cryopreserved bacterial cultures of reference and clinical strains were streaked for isolation on appropriate agar medium (i.e., Trypticase Soy Agar, Trypticase Soy Agar with defibrinated sheep erthrocytes, Brain Heart Infusion Agar, Chocolate Agar). Following incubation to allow formation of colonies, these plates were sealed with parafilm and stored refrigerated for up to two weeks. For preparation of assay inocula and to ensure low variability, several colonies from a bacterial isolate cultured on the agar plates were pricked with an inoculating loop and aseptically transferred to Mueller-Hinton Broth (supplemented with divalent cations to required levels based on manufacturer's certification). The broth culture was grown overnight at 35° C., diluted in fresh prewarmed broth and grown to log phase; this is equivalent to a 0.5 MacFarland standard or 1×10$^8$ colony forming units per milliliter (CFU/mL). Not all cell suspensions, due to species variability, contained 1×10$^8$ CFU/mL when turbidity is equivalent to the MacFarland standard, therefore acceptable adjustments (based on NCCLS guidelines) were made in dilutions of different bacterial strains. The inoculum was diluted such that 100 μL of this culture in Mueller-Hinton Broth, supplemented Mueller-Hinton Broth, or *Haemophilus* test medium, when over layered onto a 2-fold serially diluted series of antibiotic concentrations also in 100 μL of corresponding medium, in a 96-well microtiter plate resulted in a starting bacterial concentration of 5×10$^5$ CFU/mL. The plates were then incubated 18-24 hours at 35° C. The MIC was read visually as the lowest concentration well with no bacterial growth. Bacterial growth is defined as more than three pinpoint colonies, a button of precipitated cells larger than 2 mm in diameter, or obvious turbidity.

Strains routinely tested in the initial screen included methicillin-sensitive *Staphylococcus aureus* ORSSA), methicillin-resistant *Staphylococcus aureus* (MRSA), *Staphylococcus aureus* producing penicillinase, methicillin-sensistive *Staphylococcus epidermidis* (MSSE), methicillin-resistant *Staphylococcus epidermidis* (MRSE), vancomycin-sensitive *Enterococcus faecium* (EFMVS), vancomycin-sensitive *Enterococcus faecalis* (EFSVS), vancomycin-resistant *Enterococcus faecium* also resistant to teicoplanin (EFMVR Van A), vancomycin-resistant *Enterococcus faecium* sensistive to teicoplanin (EFMVR Van B), vancomycin-resistant *Enterococcus faecalis* also resistant to teicoplanin (EFSVR Van A), vancomycin-resistant *Enterococcus faecalis* sensitive to teicoplanin (EFSVR Van B), penicillin-sensitive *Streptococcus pneumoniae* (PSSP) and penicillin-resistant *Streptococcus pneumoniae* (PSRP). Because of the inability of PSSP and PSRP to grow well in Mueller-Hinton broth, MICs with those strains were determined using either TS broth supplemented with defibrinated blood or *Haemophilus* test medium.

Test compounds having significant activity against the strains mentioned above were then tested for MIC values in a larger panel of clinical isolates including the species listed above as well as non-speciated coagulase negative *Staphylococcus* both sensitive and resistant to methicillin (MS-CNS and MR-CNS). Additionally, these test compounds were also assayed for MICs against gram-negative microorganisms, such as *Escherichia coli*, *Pseudomonas aeruginosa*, *Klebsiella pneumoniae*, *Enterobacter cloacae*, *Acinetobacter baumannii*, *Haemophilus influenzae* and *Moraxella catarrhalis*.

Table II shows MIC$_{90}$ data for a compound of this invention against methicillin-resistant *S. aureus* (MRSA) and methicillin-resistant *S. epidermitis* (MRSE) as compared to the known antibiotic, vancomycin.

TABLE II

Minimum Inhibitory Concentrations (MICs)

| Microorganism | Test Compound | MIC$_{90}$[2] (μg/mL) |
|---|---|---|
| Methicillin-resistant *S. aureus* (MRSA) (n = 53)[1] | Compound 1 | ≦0.1 |
|  | Vancomycin | 3 |
| Methicillin-resistant *S. epidermitis* (MRSE) and other coagulase-negative staphylococci (n = 34) | Compound 1 | ≦0.1 |
|  | Vancomycin | 4 |

[1]Number of strains tested.
[2]Minimum inhibitory concentration for 90% of strains tested.

Additionally, as shown in Table III, compounds of this invention also had surprising and unexpected MICs against various methicillin-resistant *S. aureus* strains when compared to a related des-chloro derivative (i.e., Compound 34).

TABLE III

Minimum Inhibitory Concentrations

|  | MIC (μg/mL) | |
|---|---|---|
| Microorganism | Cmpd. 1 | Cmpd. 34 |
| MRSA 33591 | ≦0.1 | 0.17 |
| MRSA MED-103 | ≦0.1 | 0.20 |
| MRSA MED-104 | 0.10 | 0.58 |
| MRSA MED-107 | ≦0.1 | 0.34 |
| MRSA MED-110 | 0.20 | 0.49 |
| MRSA MED-572 | ≦0.1 | <0.1 |
| MRSA MED-84 | ≦0.1 | 0.29 |

TABLE III-continued

Minimum Inhibitory Concentrations

| | MIC (µg/mL) | |
|---|---|---|
| Microorganism | Cmpd. 1 | Cmpd. 34 |
| MRSA MED-85 | ≦0.1 | 0.32 |
| MRSA MED-86 | ≦0.1 | 0.29 |
| MRSA MED-87 | ≦0.1 | 0.49 |
| MRSA MED-88 | ≦0.1 | 0.34 |
| MRSA MED-89 | ≦0.1 | 0.18 |

Example 36

Time-Kill Assay

This time-kill assay is a method for measuring the rate of bactericidal activity of a test compound. These procedures are similar to those described in V. Lorian, "Antibiotics in Laboratory Medicine", Fourth Edition, Williams and Wilkins (1996), pages 104-105. A rapid time-kill is desirable to quickly prevent bacterial colonization and reduce host tissue damage.

Bacterial inocula were prepared as described in Example 35 for determination of MIC. Bacteria were diluted in prewarmed media in shake flasks and incubated with shaking (200 rpm, 35° C.). At 0, 1, 4, and 24 hours samples were withdrawn from the flasks and bacteria were enumerated by plate counting. Subsequent to the initial sampling, a compound to be assayed was added to the shake flask culture. Plate counts at these intervals previous to and following addition of the compound were expressed graphically in a time-kill curve. Bactericidal activity is defined as a ≧3 log decrease (reduction greater than or equal to 99.9%) in bacterial cell numbers by 24 hours.

In this assay, a compound of formula I, i.e., Compound 1, was bactericidal against MSSA 13709 and MRSA 33591 at a concentration of ≦1 µg/mL in 4 hours. By comparison, vancomycin was bactericidal against MSSA 13709 and MRSA 33591 at a concentration of 4 µg/mL in 24 hours.

Example 37

In Vivo Efficacy Studies in Neutropenic Mice

Animals (male CD-1 mice, 20-30 g) were acquired from Charles Rivers Laboratories (Gilroy, Calif.) and allowed access to food and water ad libitum. Neutropenia was induced via 200 mg/kg intraperitoneal (IP) injection of cyclophosphamide given four and two days prior to the inoculation of bacteria.

The organism used was either a susceptible or resistant strain of clinically relevant gram positive pathogens, such as methicillin-susceptible *Staphylococcus aureus* ORSSA 13709) and methicillin-resistant *Staphylococcus aureus* (MRSA 33591). The bacterial inoculum concentration was ~$10^6$ CFU/mL. Animals were lightly anesthetized with isoflurane and 50 mL of the bacterial inoculum was injected into the anterior thigh. One hour after the inoculation, animals were dosed intravenously with vehicle or the appropriate dose of the test compound. At 0 hours and 24 hours post-treatment, the animals were euthanized ($CO_2$ asphyxiation) and the anterior and posterior thigh collected aseptically. The thigh was placed into 10 mL sterile saline and homogenized. Dilutions of the homogenate were plated onto triptic soy agar plates which were incubated overnight. The number of bacterial colonies on a given plate was multiplied by the dilution factor, divided by the thigh weight (in grams) and expressed as log CFU/g. $ED_{50}$ (dose required to produce 50% of the maximum reduction in thigh titre) was estimated for each test compound.

In this assay using MRSA 33591, a compound of formula I, i.e., Compound 1, had an $ED_{50}$ of <0.20 mg/kg, iv, compared to an $ED_{50}$ of 9 mg/kg, iv, for vancomycin.

Example 38

Determination of Aqueous Solubility

The aqueous solubility of a compound of this invention was determined using the following procedure. A 5 wt. % dextrose buffer solution at pH 2.2 was prepared by adding 1 mL of 1 N hydrochloric acid (Aldrich) to 99 mL of a 5 wt. % aqueous dextrose solution (Baxter).

A 1 mg/mL stock solution for calibration standards was then prepared by dissolving 1 mg of the test compound in 1 mL of DMSO. This solution was vortexed for 30 seconds and then sonicated for 10 minutes. The stock solution was then diluted with water to prepare calibration standards having the following concentrations: 50, 125, 250, 375 and 500 ug/mL.

Each test compound (30 mg) was weighed into a Millipore non-sterile, Ultrafree-MC 0.1 um filter unit (Millipore UFC30VVOO) and a magnetic stir bar was added to each unit. The 5 wt. % dextrose buffer solution (750 uL) was then added to each unit and these mixtures were vortexed for 5 minutes. The filter units were then placed in an Eppendorf tube rack and the tube rack was placed on top of a magnetic stirrer. Each unit was then titrated to pH 3 using 1 N NaOH (VWR) and the resulting solutions centrifuged at 7000 rpms for 5 minutes. Each unit was then diluted 200 fold with 5% dextrose buffer solution and the diluted samples were transferred into auto sampler vials for analysis.

The calibration standards and the test samples were analyzed by reverse-phase HPLC using the following conditions:

Column: Luna 150×4.6 mm; C18; 5u

Mobile phase: A=5/95, B=95/5, both=MeCN/$H_2O$; 0.1% TFA

Method: 10 m Lido 100 (0-100% B in 6 min)

Injection volume: 20 uL

Wavelength: 214 nm

The solubility of each test sample was calculated by comparing the peak area of the test sample to the calibration curve and multiplying by the dilution factor. Using the above procedure with duplicate sample preparations, Compound 1 was found to have a solubility of >47.9 mg/mL.

While the present invention has been described with reference to specific embodiments thereof, it should be understood by those skilled in the art that various changes may be made an equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited herein are incorporated by reference herein in their entirety to the same extent as if they had been individually incorporated by reference.

What is claimed is:
1. A compound of the formula:
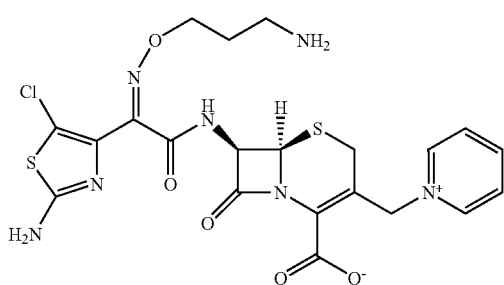
or a salt thereof.
2. A hydrochloride salt of a compound compound of the formula:
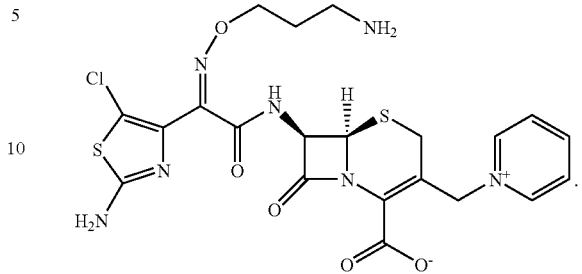
* * * * *